United States Patent [19]
McCapra et al.

[11] Patent Number: 5,284,951
[45] Date of Patent: Feb. 8, 1994

[54] HYDROLYTICALLY STABLE CHEMILUMINESCENT LABELS AND THEIR CONJUGATES, AND ASSAYS THEREFROM

[75] Inventors: Frank McCapra, Seaford, Great Britain; Iraj Beheshti, Edina, Minn.

[73] Assignee: London Diagnostics, Inc., Eden Prairie, Minn.

[21] Appl. No.: 859,956

[22] Filed: Mar. 30, 1992

Related U.S. Application Data

[63] Continuation-in-part of Ser. No. 140,040, Dec. 31, 1987, abandoned, and Ser. No. 291,843, Dec. 29, 1988, abandoned, and Ser. No. 418,956, Oct. 10, 1989, abandoned.

[51] Int. Cl.$^5$ ............................................ C07D 219/04
[52] U.S. Cl. .................................. 546/107; 436/501; 530/409; 544/355; 546/61; 546/79; 546/93; 546/102; 546/107; 546/108; 546/112; 546/147; 546/170; 548/309.4
[58] Field of Search .................. 546/79, 93, 102, 104, 546/107, 108, 61, 112, 147, 170; 436/501; 530/409; 544/355

[56] References Cited

U.S. PATENT DOCUMENTS

| | | | |
|---|---|---|---|
| 3,352,791 | 11/1967 | Sheehan et al. | 546/102 X |
| 3,689,391 | 9/1972 | Ullman | 546/102 X |
| 4,745,181 | 5/1988 | Law et al. | 546/104 X |
| 4,918,192 | 4/1990 | Law et al. | 546/104 |
| 4,946,958 | 8/1990 | Campbell et al. | 546/104 |
| 4,950,613 | 8/1990 | Arnold et al. | 546/104 |
| 5,110,932 | 5/1992 | Law et al. | 546/102 |

FOREIGN PATENT DOCUMENTS

| | | | |
|---|---|---|---|
| 216553 | 4/1987 | European Pat. Off. | 546/102 |
| 324202 | 7/1989 | European Pat. Off. | 546/102 |
| 330050 | 8/1989 | European Pat. Off. | 546/104 |
| 361817 | 4/1990 | European Pat. Off. | 546/102 |
| 1461877 | 1/1977 | United Kingdom | 546/102 |

*Primary Examiner*—Richard L. Raymond
*Attorney, Agent, or Firm*—George A. Skoler

[57] ABSTRACT

A novel chemiluminescent labeling compositions comprising an ester, thioester or amide covalently and jointly bonded to (1) a carbon of a heterocyclic ring or ring system that is susceptible to attack by peroxide or molecular oxygen and (2) an aryl ring or ring system wherein the heterocyclic ring or ring system is distinguished by a heteroatom thereof in an oxidation state which causes the attacked carbon atom to form an intermediate that decays and produces chemiluminescence; the aryl ring or ring system contains at least three substituents on a six-member aromatic hydrocarbon that together sterically and electronically hinder hydrolysis of the linkage, which substituents involve ortho substituent groups on the aryl in conjunction with meta and/or para substituents thereon that possess an electron withdrawing capacity characterized as a $\sigma_p$ value greater than 0 and less than 1. Included are the chemiluminescent labeling composition conjugated with a specific binding material; a chemiluminescent assay comprising the conjugate; and a chemiluminescent assay kit comprising the conjugate with the capability of conducting the assay.

18 Claims, No Drawings

HYDROLYTICALLY STABLE CHEMILUMINESCENT LABELS AND THEIR CONJUGATES, AND ASSAYS THEREFROM

RELATED APPLICATIONS

This application is a continuation-in-part of application Ser. No. 140,040, filed Dec. 31, 1987, now abandoned copending application Ser. No. 291,843, filed Dec. 29, 1988, now abandoned, and copending application Ser. No. 418,956, filed Oct. 10, 1989, now abandoned.

BRIEF DESCRIPTION OF THE INVENTION

This invention relates to unique chemiluminescent labeling compounds, conjugates containing associated versions of the labeling compounds, assays and kits for performing such assay utilizing the conjugates. The labeling compounds contain special sterically-hindered aryl heterocyclic esters, thiolesters and amides.

BACKGROUND TO THE INVENTION

The literature describes classes of compounds that give off light or "luminesce" by reaction through chemical treatment, e.g., with peroxide or molecular oxygen at high pH. The compounds that have this capability are termed chemiluminescent materials. Light is produced by the decay of the transient ("intermediate") structure formed by peroxide or molecular oxygen induced reaction at an $sp^2$ or $sp^3$ hybridized carbon in the compound that is part of a chain or a ring or ring system.

As the literature indicates, any series of reactions which produce the intermediate:

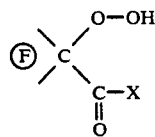

will lead to moderate to strong chemiluminescence. $\text{\textcircled{F}}$ is a structure such that the product carbonyl derivative

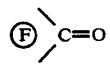

is fluorescent and X is a good leaving group, usually with XH, for efficient chemiluminescence, having a $pK_a$ of about $\leq 11$, preferably $<11$, and most preferably, from about 5 to about 8. The reaction may require base catalysis.

The intermediate can be prepared (in isolable or transient form, depending on $\text{\textcircled{F}}$) from species such as:

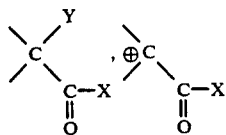

and $H_2O_2$ (Y is halogen, $-OSO_2R$, and the like) or

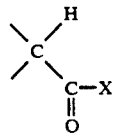

and base/$O_2$.

See *Endeavour*, 23, No. 117 (1973) p. 140, *The Chemistry of Bioluminescence* in "*Bioluminescence in Action*" (P. J. Herring, ed.), Academic Press, London, 1978 (pp. 64–5), *Proc. R. Soc. Lond.*, B 215, p. 256 (1982), *Progress in Organic Chemistry*, (W. Carruthers and J. K. Sutherland, eds.), Butterworth, London (1973), p. 261, all authored by F. McCapra.

For example, chemiluminescent aryl esters that contain such hybridized carbon, termed a labeling compound, react according to the following general reaction:

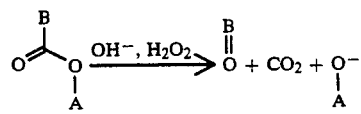

where A is an aryl ring or ring system and B is a heterocyclic ring or ring syste. In this reaction, —O—A, the leaving group, is cleaved by perhydrolysis resulting in steps leading to the transient intermediate, B=O, that proceeds to decay generating luminescence.

The characteristics of some of these chemiluminescent compounds, their chemistry of manufacture, and other factors relating to them, are more fully described by McCapra, "Chemiluminescence of Organic Compounds," in Progress in Organic Chemistry, vol. 8, Carruthers and Sutherland ed., Wiley & Sons (1973); Kohen, Bayer, Wilechek, Barnard, Kim, Colleins, Beheshti, Richardson and McCapra, "Development Of Luminescence-Based Immunoassays For Haptens And For Peptide Hormones," pp. 149–158, in *Analytical Applications Of Bioluminescence and Chemiluminescence*, Academic Press, Inc. (1984); Richardson, Kim, Barnard, Collins and McCapra, *Clinical Chemistry*, vol. 31, no. 10, pp. 1664–1668 (1985); McCapra, "The Application of Chemiluminescence in Diagnostics," 40th Conference of the American Association of Clinical Chemists, New Orleans, La., Jul. 28, 1988; McCapra, "The Chemiluminescence Of Organic Compounds," Quarterly Reviews, vol. 20, pp. 485–510 (1966); McCapra, "The Chemiluminescence Of Organic Compounds," *Pure and Applied Chemistry*, vol. 24, pp. 611–629 (1970); McCapra, "The chemistry of bioluminescence," *Proceedings Of Royal Society*, vol. B215, pp. 247–278 (1982); McCapra and Beheshti, "Selected Chemical Reactions That Produce Light," *Bioluminescence and Chemiluminescence: Instruments and Applications*, CRC Press, vol. 1, Chapter 2, pp. 9–37 (1985); McCapra, "Chemiluminescent Reactions of Acridines," Chapt. IX, *Acridines*, R. M. Acheson, Ed., pp. 615–630, John Wiley & Sons, Inc. (1973); McCapra, "Chemical Mechanisms in Bioluminescence," *Accounts Of Chemical Research*, vol. 9, no. 6, pp. 201–208 (June 1976); and in many other publications and presentations on the subject.

As noted in the above literature, chemiluminescent compounds of a variety of structures have been projected as labels for a variety of assays including immunoassays (in this respect, see U.S. Pat. Nos. 4,383,031, 4,380,580 and 4,226,993). The esters, thiolesters and amides, alone or conjugated (i.e., chemically coupled to another material), are especially desirable forms of chemiluminescent labels. However, they lose their luminescence capability over time in an aqueous system because they hydrolyze to products that are not available to the assay. Until recently, these compounds have not been used in commercial assays. Until this invention, ester, thiolester and amide forms of this class of materials lacked sufficient hydrolytic stability to be stored in the most convenient form over an extended period of time, which is as a component of an aqueous system.

It is well understood in chemistry that carboxylic acid esters, thiolesters and amides are susceptible to hydrolytic attack resulting in the formation of the carboxylic acid and the hydroxy, mercapto or amino component that is the theoretical or actual precursor to the ester, thiolester or amide. Hydrolysis is more pronounced under acid or basic conditions. It is also recognized in chemistry that certain levels of hydrolysis can be inhibited by the inclusion of properly positioned bulky groups that chemically sterically hinder those linkages, see Nishioka et al., *J. Org. Chem.*, vol. 40, no. 17, pp. 2520–2525 (1975), Fujita et al., "The Analysis of the Ortho Effect," *Progress in Physical Organic Chemistry*, 8, pp. 49–89 (1976), Morrison and Boyd, *Organic Chemistry*, 5$^{th}$ Ed., pp. 842–843 (1987) and March, *Advanced Organic Chemistry*, 3rd Ed., page 240 (1985). According to March:

"Another example of steric hindrance is found in 2,6-disubstituted benzoic acids, which are difficult to esterify no matter what the resonance or field effects of the groups in the 2 or the 6 position. Similarly, once the 2,6-disubstituted benzoic acids are esterified, the esters are difficult to hydrolyze." (Emphasis in the original)

The difficulty in esterification is not the same in making esters from 2,6-substituted phenols, but the general principles described by March are applicable to enhancing the hydrolytic stability of the resultant ester so long as the ortho substitutions are electron donating. As this invention demonstrates, effective levels of hydrolytic stability require the presence of a select level of electron withdrawing chemical effect in conjunction with (and in addition to) traditional chemical steric hindrance factors.

The functional electron withdrawing or electron donating characteristics of a group in an organic compound is conventionally measured relative to hydrogen. This relative ranking accepts that all groups on a molecule will provide some electron withdrawing effect, and distinquishes them by the nature of impact the group has on the molecule's performance. An electron withdrawing functional group, characterized by a positive number, will draw electrons to itself more than hydrogen would if it occupied the same position in the molecule. The opposite occurs with an "electron donating group," a lesser electron withdrawing group which chemical convention characterizes by a negative number. Sigma para values ($\sigma_p$) are the relative measurement of electron withdrawing or electron donating qualities of a functional group in the para position on benzoic acid. See March, *Advanced Organic Chemistry*, 3rd Edition, Publ. by John Wiley & Sons, New York, N.Y. (1985) at pp. 242–250 and 617-8. Tables of $\sigma_p$ values for various groups can be found in Hansch et al., *J. Med. Chem.* 16(11):1209–1213 (1973) and Hansch and Leo, "Substituent Constants for Correlation Analysis in Chemistry and Biology," Ch. 6, pp. 49–52 (John Wiley & Sons, New York 1979). The $\sigma_p$ values reported in the Hansch articles are relied on herein in characterizing relative values for groups both in the meta and para position.

The function of chemiluminescent labels in assay applications involves the coupling of the label compound to a substrate molecule. Such coupling can be achieved by solvent interraction (e.g., molecular compatibility), any heterolytic or homolytic mechanism induced by chemical means and influenced by physical effects, such as time, temperature and/or mass action. For example, the reaction can be nucleophilic or electrophilic, or it can involve free radical mechanisms. In the broadest perspective, the coupling can be viewed as achievable via strong to weak bonding forces.

A chemiluminescent label in assays is an associated moiety of a binding material. The moiety is derived from a chemical compound which, as such, possesses chemiluminescent capabilities. Hereinafter, the term moiety as applied to the label as such, is a reference to the compound prior to being associated with a binding material. The term associated is intended to include all or any of the mechanisms for coupling the label to the substrate molecule.

The term "functional" in chemistry typically refers to a group that influences the performance of a chemical or constitutes the site for homolytic or heterolytic reactions. For example, a functional alkyl substituent, used in the context of interreactions through that substituent, means an alkyl group substituted so that it can effect that reaction. But an alkyl group termed functional for the electronic effects it induces in the molecule is a reference to the alkyl group per se.

THE INVENTION

This invention relates to unique chemiluminescent labeling compounds, conjugates containing associated versions of the labeling compounds, assays and kits for performing such assay utilizing the conjugates. The labeling compounds contain special sterically-hindered aryl heterocyclic substituted esters, thiolesters and amides.

This invention relates to novel chemiluminescent labeling compositions and their conjugates with specific binding materials that are normally maintained in an aqueous medium. These compositions and the conjugates find special application in specific binding assays because the chemiluminescent compound, i.e., the labeled moiety, has increased and unique stability in aqueous mediums and exceptional light emitting qualities.

The novel root compound of the invention is a chemiluminescent compound characterized by the presence an aryl ester, thiolester or amide of a carboxylic acid substituted heterocyclic ring that is susceptible to chemical attack (such as by oxidic attack) to form a transient compound from the heterocyclic ring. The heterocyclic ring is ring carbon-bonded to the carbonyl of the ester, thiolester and amide moiety and possesses a heteroatom in an oxidation state that allows chemiluminescence by dissociating a compound at the carbon bonded to the carbonyl ("intermediate") that decays to produce chemiluminescence. The aryl ring or ring system is ring carbon-bonded to the oxygen, sulfur or nitrogen of the ester, thiolester or amide, as the case may be, and contains at least three substituents on a six-member ring.

The substitution on the six-member ring comprises three or more groups acting in concert to sterically and electronically hinder hydrolysis of the ester, thiolester or amide linkage. Significant to this invention is the presence of diortho electron donating substitution on the aryl unit in conjunction with meta and/or para substituents that possess a specific level of electron withdrawing capacity. That specific level of electron withdrawing capacity is a $\sigma_p$ value greater than 0 and less than 1. It is this combination that causes the chemiluminescent label compound to have uniquely high hydrolytic stability that is superior to the use of meta and/or para substituents that possess a $\sigma_p$ value of 0 and less than 0 or 1 and greater than 1.

Also in accordance with the present invention are conjugates of the labeling composition, assay systems utilizing the conjugates, and assay kits incorporating such chemiluminescent labels.

In particular, this invention relates to a hydrolytically stable heterocyclic composition capable of chemiluminescent properties when labeled (i.e., affixed as a label) to a specific binding material by chemically-induced reaction, comprising
(a) an aryl ring,
(b) a sterically-hindered ester, thiolester or amide linkage moiety with enhanced hydrolytic stability, and
(c) a heterocyclic organic ring moiety, in which
  (1) the carbonyl carbon of (b) is covalently bonded to a carbon atom (x) of (c) and the remaining free valence of (b) is carbon bonded to an aromatic ring carbon atom (y) of (a),
  (2) (a) contains at least three substituent groups hindering hydrolysis of (b), two of which are electron donating and located on the ring carbon atoms adjacent to (y), the remainder are meta and/or para to (y) and electron withdrawing with a $\sigma_p$ value greater than 0 and less than 1, and
  (3) (c) contains
    (i) at least one ring carbon atom adjacent to said ring carbon atom (x), and
    (ii) a ring member heteroatom in an oxidation state that provides such chemiluminescence properties.

Also, this invention contemplates hydrolytically stable conjugates possessing chemiluminescent properties by chemical reaction, comprising a chemiluminescent label bonded to a specific binding material that contains
(a) an aryl ring,
(b) a sterically-hindered ester, thiolester or amide linkage moiety with enhanced hydrolytic stability, and
(c) a heterocyclic organic ring moiety, in which
  (1) the carbonyl carbon of (b) is covalently bonded to a carbon atom (x) of (c) and the remaining free valence of (b) is carbon bonded to an aromatic ring carbon atom (y) of (a),
  (2) (a) contains at least three substituent groups hindering hydrolysis of (b), two of which are electron donating and located on the ring carbon atoms adjacent to (y), the remainder are meta and/or para to (y) and electron withdrawing with a $\sigma_p$ value greater than 0 and less than 1, and
  (3)(c) contains
    (i) at least one ring carbon atom adjacent to said ring carbon atom (x), and
    (ii) a ring member heteroatom that is in an oxidation state whereby reaction of molecular oxygen or a peroxide with said composition forms an intermediate which decays to produce chemiluminescence.

The invention encompasses a method for assaying the presence of an analyte in a sample. The method comprises contacting an analyte with the aforementioned chemiluminescent-labeled specific binding material (the "conjugate"), inducing chemiluminescence by decay of an intermediate dissociated from the conjugate, and measuring luminescence therefrom to assay the analyte.

In keeping with the inventive chemiluminescent-label's function of assaying, the invention embodies a specific binding assay kit comprising a vial containing a conjugate possessing chemiluminescent properties by chemically induced reaction and containing the aforementioned chemiluminescent label bonded to a specific binding material.

The invention recognizes that hydrolytic stability of a chemiluminescent label composition that utilizes aryl ester, thiolesters, and amides, as defined herein, linked to heterocyclic carboxy compounds, is affected by two factors. The first is the utilization of diortho substitution on the aryl ring of a kind that traditionally contributes to hydrolytic stability. This is the "bulky group" steric hindrance effect noted by Morrison and Boyd, supra. In the context of sigma values, these bulky groups are typically classed as electron donating. The second is the utilization of meta and/or para substitution on the same ring that untraditionally contributes to hydrolytic stability. This latter substitution possesses a $\sigma_p$ value greater than 0 and less than 1, as bonded to the ring. This combination of steric hindrance and positive $\sigma_p$ value provides materially superior hydrolytic stability to the labeling composition than substituents that possess a $\sigma_p$ value of 0 or less than 0, and 1 or more than 1.

DETAILED DESCRIPTION OF THE INVENTION

As mentioned above, proper positioning of bulky groups in an ester enhances the ester's hydrolytic stability. In the case of an aryl ester, steric hindrance is expected with bulky groups that block the ester moiety. Those groups may be provided on the aryl group in the ortho positions relative to the juncture with the ester moiety. Groups that may be dormant to any other reaction may not provide steric hindrance because of its chemical nature. For example, a group in a position alpha to a carbonyl moiety of an ester group that is electron withdrawing (such as an alpha chloro group) could adversely affect the hydrolytic stability of the ester group. However, a methyl electron donating group in the same position enhances hydrolytic stability. Thus, the relative position of the bulky group and its chemical nature is important to steric hindrance. As a result, the typical bulky group provided in the ortho position of an aryl ester for steric hindrance is electron donating. An electron withdrawing group would be expected to adversely affect the hydrolytic stability of the aryl ester. The presence of an electron withdrawing group substituted on an aryl ester would be expected to, to some degree, as a result of the field effects they introduce, reduce the hydrolytic stability of the ester, even if it is otherwise substituted with electron donating groups in the ortho positions. The presence of the electron withdrawing group would be expected to reduce the electron flow provided by the ortho electron donating groups to the ester group.

It has been surprisingly found that the presence of electron donating groups having a $\sigma_p$ value greater than 0 and less than 1, in aryl esters in positions meta and/or para to the ester linkage contribute significantly to the hydrolytic stability of the ester group. The following experiments demonstrates this point.

A small amount (about 0.1 mg) of a substituted phenyl ester of acridinium carboxylate fluorosulfonate chemiluminescent label, depicted in the following table, was dissolved in 100 μl of N,N-dimethylformamide (DMF). This solution was serially diluted (in the v/v ratio of 1:100) in a pH 6.0 phosphate buffer containing 0.4% BSA (bovine serum albumin) and 0.001% Thimerosal ®, as preservative. Chemiluminescent counts between 100,000 and about 400,000 were obtained. About 2 to 5 ml were incubated at 37° C. in a clear 5 ml vial capped with a rubber stopper and wrapped with Parafilm ®. Three 20 μl samples of each label were counted in a Berthold ® luminometer that was checked at various time intervals in the course of 14 days. The percent recovery of chemiluminescent counts after 14 days is set forth in the following table, as well as the relative ratio against a $\sigma_p$ value of 0:

| $-R^8 =$ | % Recovery | Relative Ratio Against #7 | Sigma$_p$ Value |
|---|---|---|---|
| 1  3,5-dimethyl-4-nitrophenyl | 86 | 1.34 | 0.78 |
| 2  3,5-dimethyl-4-bromophenyl | 82 | 1.28 | 0.23 |
| 3  3,5-dimethyl-4-(sulfonamido-glycine benzyl ester)phenyl | 81 | 1.27 | 0.57 |
| 4  3,5-dimethyl-4-sulfonatophenyl | 76 | 1.19 | 0.09 |
| 5  3,5-dimethyl-4-(benzyloxycarbonyl)phenyl | 72 | 1.13 | 0.45 |

| −R⁸ = | % Recovery | Relative Ratio Against #7 | Sigma$_p$ Value |
|---|---|---|---|
| 6 (3,5-dimethylbenzoate) | 72 | 1.13 | 0.00 |
| 7 (2,3-dimethylphenyl) | 64 | 1.00 | 0.00 |
| 8 (3,5-dimethylphenyl propyl benzyl ester) | 69 | 1.06 | −0.07 |
| 9 (3,4,5-trimethylphenyl) | 65 | 1.02 | −0.17 |

The data in the above table show the trend that significantly higher chemiluminescent count is obtainable with 2,6-dimethyl m or p substituted phenyl ester where the substitution has a $\sigma_p$ value greater than 0. Though compounds 3 and 8 differ materially in hydrolytic stability, they each contain large substituents in the meta or para position. In the case of compound 3, the sulfonamide linkage within the large substituent provides a high $\sigma_p$ value of 0.4, and in the case of compound 8, the propyl bridge to the ester contributes to electron donation, hence a $\sigma_p$ value of −0.07. With respect to compound 5, its high $\sigma_p$ value of 0.45 coupled with the % Recovery value strongly suggests that the ester hydrolyzed under the conditions of the experiment.

The chemiluminescent compounds of the present invention have the following schematic formula:

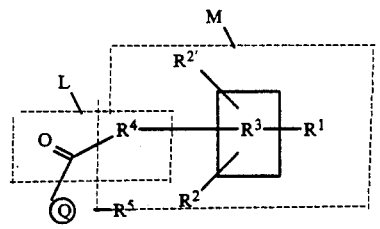

I.

In schematic formula 1., the hatched-line box labeled "L" contains the ester, thiolester or amide "linkage" which is carbon-bonded between two substituted rings or ring systems represented by the circle labeled "Q" and the solid box labeled "R³". Whether the linkage L is an ester, thiolester or amide is determined by R⁴ being —O—, —S— or —NT—, respectively. T is a stable nitrogen bonded group such as —SO₂CF₃, to form —N(SO₂CF₃)— and equivalent groups. The preferred linkage is the ester. M encompasses the leaving group comprising a portion of L and moiety R³ with its associated R¹, R² and R²'. M would be the leaving group even if R¹ were conjugated to a specific binding material.

The leaving group possesses the typical $pK_a$ of about $\leq 11$.

Q is a heterocyclic ring or ring system to which the ester, thiolester or amide linkage L is attached at a carbon atom within the heterocyclic ring or ring system. That carbon atom (1) is either $sp^2$ or $sp^3$ hybridized, and (2) is susceptible to attack by peroxide or molecular oxygen to form the intermediate that decays to produce chemiluminescence. The oxidation state of the heteroatom within the heterocyclic ring or ring system will determine whether the carbon atom is susceptible to such attack. If the carbon to which the linkage is attached is $sp^2$ hybridized, the heteroatom is in a positive oxidation state (i.e., have a positive charge, for example, as obtained by N-alkylation or N-oxidation). If the carbon to which the linkage is attached is $sp^3$ hybridized, the heteroatom is in a neutral oxidation state (i.e., uncharged). When the heteroatom is nitrogen, proper oxidation states can be achieved only if the nitrogen is substituted with an alkyl group (including a reactive functionalized alkyl group), an aryl group (including a reactive functionalized aryl group), —O— (if the nitrogen is in a positive oxidation state) or —OH (if the nitrogen is in a neutral oxidation state). When the heteroatom is in these "proper" oxidation states, the carbon atom will be susceptible to attack by peroxide or molecular oxygen to produce the chemiluminescent intermediate.

Heterocyclic rings or ring systems that contain the heteroatom in a positive oxidation state include without limitation acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium. Rings or ring systems in which the heteroatom is in a neutral oxidation state include the reduced forms of the foregoing. These rings or ring systems are derived from the following rings or ring systems:

Acridine Series

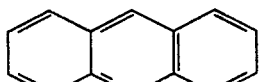

Acridine

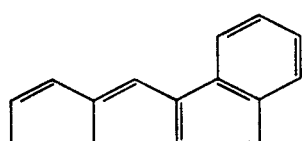

Benz[a]acridine

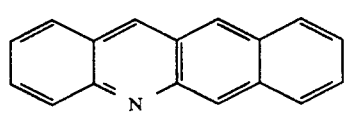

Benz[b]acridine

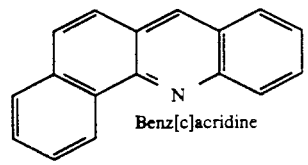

Benz[c]acridine

Azole Series

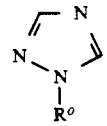 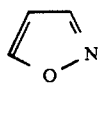

1, 2, 4-Triazole    Isooxazole

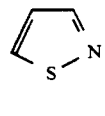 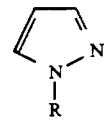

Isothioazole    1,2-Azole

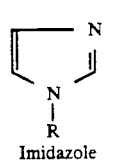 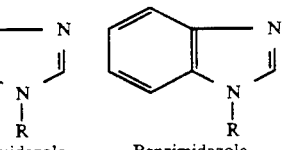

Imidazole    Benzimidazole

Quinoline Series

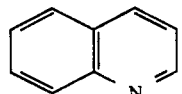 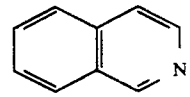

Quinoline    Isoquinoline

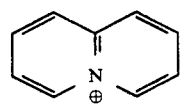

Quinolixinium Cations

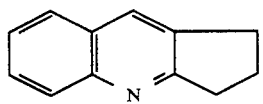

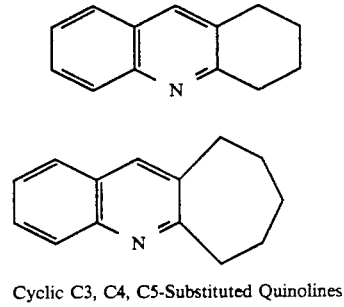

Cyclic C3, C4, C5-Substituted Quinolines

Pyridine/Pyrimidine Series

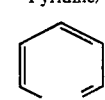 

Pyridine    Pyrimidine

-continued

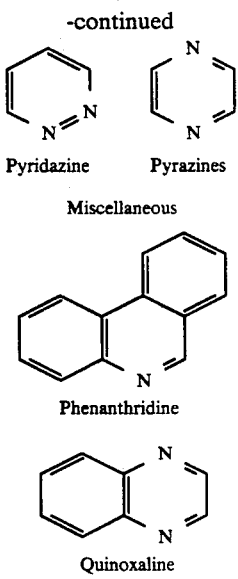

Pyridazine   Pyrazines

Miscellaneous

Phenanthridine

Quinoxaline

The aryl ring or ring system, represented by $R^3$, includes at least one substituted six-member ring of the formula

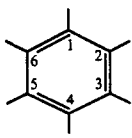

in which the substituents comprise at least one $R^1$ at ring carbons 3, 4 and 5, and $R^2$ and $R^{2'}$ at ring carbons 2 and 6. The ester, amide or thiolester linkage is directly attached through a covalent bond to such six-member ring at ring carbon 1. $R^3$ may include but is not limited to phenyl, naphthyl and anthracyl, which are derivatives of the following structures:

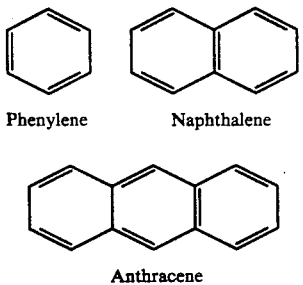

Phenylene   Naphthalene

Anthracene

In those cases where napthyl or anthracyl rings are employed, one of the rings constitutes $R^3$ and the other ring or rings in combination with it are formed via ring carbons thereof other than carbon 1. $R^3$ linked through carbon 1 may be substituted at any aromatic carbon position provided carbon atoms 2 and 6 are appropriately substituted with electron donating groups and one or more of carbons 3, 4 and 5 are appropriately substituted with a group having a $\sigma_p$ value greater than 0 and less than 1.

$R^3$ may include, but is not limited to, the substituent groups designated for $R^1$, $R^2$ and $R^{2'}$ described below. $R^3$ may be attached through substituents $R^1$ to protein or other material. In that case, where the attachment is via a nucleophilic substitution reaction, then the linkage unit attached to $R^3$ and the protein or other material, constitutes $R^1$, and should have a $\sigma_p$ value greater than 0 and less than 1.

$R^2$ and $R^{2'}$ are the classic bulky electron donating groups which are located on $R^3$ at $C_2$ and $C_6$ so as to sterically hinder, in the traditional manner, the hydrolysis of the linkage L between $R^3$ and the heterocyclic ring or ring system Q. Where $R^3$ is phenyl with the ester linkage being attached at position 1, $R^2$ and $R^{2'}$ are located at the ortho 2 and 6 positions. $R^2$ and $R^{2'}$ may be the same or different, and either may include:

an alkyl ($C_{1-4}$) or optionally functionalized alkyl ($C_{1-4}$) group an aryl or optionally functionalized aryl group —OR, where R is alkyl ($C_{1-4}$) or aryl
—SR, where R is alkyl ($C_{1-4}$) or aryl.

The required steric hindrance can also be provided by other rings within a multi-ring $R^3$ which are "adjacent" to the six-member ring to which the ester linkage is attached. For example, if $R^3$ is naphthyl and an ester linkage is attached at the 1 position, $R^2$ could be a methyl group at the 2 position and $R^{2'}$ is the "adjacent" ring containing carbons 7–10. In such cases, the adjacent ring is considered, in the classic sense of steric hindrance, to be an electron donating substituent (on the six-member ring within $R^3$) which sterically hinders the hydrolysis of the linkage.

$R^1$ in the preferred embodiment, possesses two (2) qualities: (1) when bonded to the aryl group $R^3$, it has the desired $\sigma_p$ value; and (2) it has a capability of entering into a bonding relationship with an active hydrogen containing group such as amino, amido, carboxyl, hydroxyl, thiol, and the like. The bonding capability of $R^1$ need only be sufficient to link the label compound to the active hydrogen containing group. Such bonding may be covalent, ionic, hydrogen and other associative bonding that would be acceptable for linking with the composition containing the active hydrogen to which bonding is desired.

Particularly desirable $R^1$ groups are those that are directly bonded to the $R^3$ ring $C_{3,4}$ *and/or* 5 atoms through a non-carbon and non-oxygen unit. The preferred $R^1$ groups contain non-carbon and non-oxygen radicals such as N, S, P, B, Si, and the like, bonded to one or more of the $C_{3,4}$ *and/or* 5 atoms or substituted alkoxy and alkyl possessing the desired $\sigma_p$ value. Each of these preferred groups frequently contain bonded to them one or more of oxo (i.e., =O), oxy (i.e., —O—), halogen, and carbon bonded organic moieties. When all of the free valences of the radicals are saturated with carbon bonded organic, then the group is an onium, such as quaternary ammonium, sulfonium, phosphonium, and the like. Desirable electron withdrawing groups include the following:

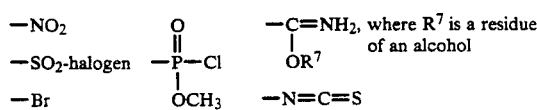

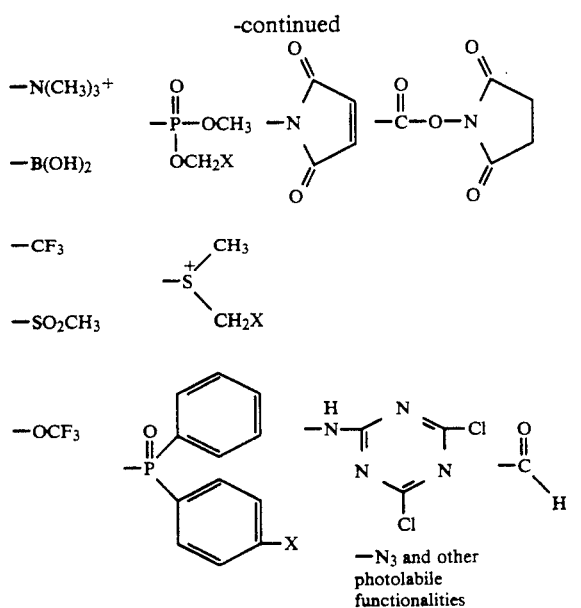
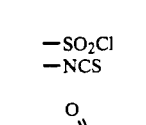
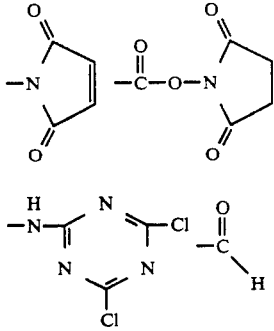

in which halogen may be fluorine, chlorine, bromine and iodine, chlorine being the most preferred, X is a functional group reactive with active hydrogen or carboxylic acid derivatives, such as carboxylic halide, sulfonyl halide, and amino. The preferred groups are $-NO_2$, $-SO_2Cl$, $-Br$, $-N(CH_3)_3{}^+$. Most preferred are $-NO_2$ and $-SO_2Cl$, the former for the uniquely high hydrolytic stability it confers to the label, per se or when conjugated, and the latter for the exceptional bonding to proteins, forming high $\sigma_p$ value stable sulfonamide bonds, and the superior hydrolytic stability conferred to the label, per se, or when conjugated.

The heterocyclic ring or ring system may contain substitutions not shown in schematic formula I. When the heterocyclic ring or ring system contains substitution, the substitution may be at any position, including the heteroatom. Such rings and ring systems, whether or not substituted, are considered herein to be within the meaning of the term "heterocyclic ring or ring system."

Suitable ring substitutions $R^5$, may be functional or non-functional. Functionality can be for the purpose of enhancing the hydrolytic stability of the compound or for providing coupling capabilities via homolytic or heterolytic reactions or other forms of association that couple the label compound to its substrate. Such substitutions include those for the purposes of producing peri-interactions around the linkage L to enhance its hydrolytic stability, providing functionality to the compound for coupling to proteins and other materials with complementary functionality, and increasing the compound's solubility and chemiluminescent efficiency. Groups useful for associating the compound to proteins and other materials so that the chemiluminescent label compounds of the invention function in a coupled state with them include, but are not limited to, the following functionally substituted moieties as $-CO_2R^6$, where $R^6$ is hydrogen, alkyl or aryl $-C=NH_2$, where $R^7$ is a residue of an alcohol
$\ \ |$
$\ \ OR^7$ or oniums (such as quaternary ammoniums, phosphoniums, sulfoniums, and the like), sugars, polyalkylenepolyamines and polyalkyleneoxide (e.g., polyoxyethylene, polyoxy-1,2-propylene, polyoxy-1,3-propylene, polyoxy-1,2-butylene, etc.), and the like. Other chains, groups and functionalities useful for attaching compounds of the present invention to protein are discussed in Ji, "Bifunctional Reagents," Meth. Enzymology 91:580 (1983), which is incorporated herein by reference. Methods of joining such attaching groups to protein and other materials utilize both covalent bonding and weaker chemical forces, and are well known in the art.

These functional groups may be bonded to the heterocyclic ring by a carbon to carbon bond, an oxygen to carbon bond, a nitrogen to carbon bond, and the like. It is desired that the hydrolytic stability of the bond to the heterocyclic ring be greater than that of the linkage achieved through reaction of the functional group and its complementary group on the substrate to which the label is being affixed.

Peri substituents, which can cause peri-interactions, include any group which can cause steric hindrance with respect to the carbon to which the ester, thiolester or amide linkage is attached and/or with respect to the carbon within the ester, thiolester of amide linkage. Preferred peri substituents include short alkyl groups ($C_{1-4}$, e.g., methyl, ethyl, and the like), aryl groups (e.g., phenyl), alkaryl (e.g., tolyl, xylyl, and the like), alkoxyalkyl ($C_{1-4}$ alkoxy, e.g., methoxymethyl, ethoxyethyl, and the like). The peri substituents, if present, are located on carbon atoms within the heterocyclic ring or ring system which are "adjacent to" the carbon to which the ester, thiolester or amide L linkage is attached. Moieties can include more than one peri substituent. For example, peri substituents can be placed in the following positions:

(a) in acridiniums and acridans: on $C_1$ and $C_8$;
(b) in phenanthridiniums and reduced phenanthridiniums: on $C_7$; and
(c) in quinoliniums and reduced quinoliniums: on $C_3$.

As noted above, covalent or ionic attachment to proteins and other materials can be effected through substitutions on $R^3$ or Q's $R^5$. Some of the electron withdrawing groups $R^1$ are particularly effective for that purpose. Of the preferred electron withdrawing groups, —SO₂Cl is exceptionally effective for attaching a chemiluminescent moiety to protein or other active hydrogen containing material. The resulting sulfonamide is possessed of the desired $\sigma_p$ value. A conjugate so formed is a particularly desirable embodiment of the invention.

The novel esters, thiolesters and amides of the invention are produced by conventional procedures in the art. For an example, a heterocyclic acyl halide of the formula

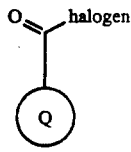

may be reacted with an aromatic 1-hydroxy, 1-mercapto or 1-amino containing the desired diortho (2,6) substitution, to form the desired L linkage. In some cases, the aromatic hydroxy, mercapto or amine will contain as well, the $R^1$ functionality. In other cases, it will be necessary to react the resultant esters, thiolesters and amides with reagents suitable for introducing the $R^1$ functionality. For example, chlorosulfonation will introduce the chlorosulfonyl groups. Its concentration in the reaction medium can be amplified by subsequent chlorination with a chlorinating agent such as thionyl chloride.

In many cases, the reactions will proceed to the formation of intermediates that require separation for the next reaction step or final products that require isolation. In such cases, conventional techniques such as distillation, extraction, crystallization, washing and the like, will be required. Conventional separation by the addition of non-solvent to a solvent solution to force precipitation of a desired material is frequently found useful.

The above-described improved chemiluminescent compounds are useful in a broad range of specific binding assays for the presence of analyte in a sample. "Presence" shall mean herein the qualitative and/or quantitative detection of an analyte. Such assays may be directed at any analyte which may be detected by use of the improved chemiluminescent compound in conjunction with specific binding reactions to form a moiety thereon. These assays include, without limitation, immunoassays, protein binding assays and nucleic acid hybridization assays.

In a typical immunoassay, the analyte is immunoreactive and its presence in a sample may be determined by virtue of its immunoreaction with an assay reagent. In a typical protein binding assay, the presence of analyte in a sample is determined by the specific binding reactivity of the analyte with an assay reagent where the reactivity is other than immunoreactivity. Examples of this include enzyme-substrate recognition and the binding affinity of avidin for biotin. In the typical nucleic acid hybridization assay, the presence of analyte in a sample is determined by a hybridization reaction of the analyte with an assay reagent. Analyte nucleic acid (usually present as double stranded DNA or RNA) is usually first converted to a single stranded form and immobilized onto a carrier (e.g., nitrocellulose paper). The analyte nucleic acid may alternatively be electrophoresed into a gel matrix. The immobilized analyte may then be hybridized (i.e., specifically bound) by a complementary sequence of nucleic acid.

The foregoing specific binding assays may be performed in a wide variety of assay formats. These assay formats fall within two broad categories. In the first category, the assay utilizes a chemiluminescent conjugate which comprises the improved chemiluminescent moiety attached to a specific binding material. "Specific binding material" means herein any material which will bind specifically by an immunoreaction, protein binding reaction, nucleic acid hybridization reaction, and any other reaction in which the material reacts specifically with a restricted class of biological, biochemical or chemical species. In this category of assays, the chemiluminescent conjugate participates in a specific binding reaction and the presence of analyte in the sample is proportional to the formation of one or more specific binding reaction products containing the chemiluminescent conjugate. The assay is performed by allowing the requisite specific binding reactions to occur under suitable reaction conditions. The formation of specific binding reaction products containing the chemiluminescent conjugate is determined by measuring the chemiluminescence of such products containing the chemiluminescent conjugate or by measuring the chemiluminescence of unreacted or partially reacted chemiluminescent conjugate not contained in such products.

This first category of assay formats is illustrated by sandwich assays, competitive assays, surface antigen assays, sequential saturation assays, competitive displacement assays and quenching assays.

In a sandwich format, the specific binding material to which the chemiluminescent moiety is attached, is capable of specifically binding with the analyte. The assay further utilizes a reactant which is capable of specifically binding with the analyte to form a reactant-analyte-chemiluminescent conjugate complex. The reactant may be attached to a solid phase, including without limitation, dip sticks, beads, tubes, paper or polymer sheets. In such cases, the presence of analyte in a sample will be proportional to the chemiluminescence of the solid phase after the specific binding reactions are completed. Such assay formats are discussed further in U.S. Pat. Nos. 4,652,533, 4,383,031, 4,380,580 and 4,226,993, which are incorporated herein by reference.

In a competitive format, the assay utilizes a reactant which is capable of specifically binding with the analyte to form an analyte-reactant complex and with the specific binding material, to which the chemiluminescent moiety is attached, to form a chemiluminescent conjugate-reactant complex. The reactant may be attached to a solid phase, or alternatively reaction products containing the reactant may be precipitated by use of a second antibody or by other known means. In this competitive format, the presence of analyte is "proportional," i.e., inversely proportional, to the chemiluminescence of the solid phase or precipitate. A further discussion of this assay format may be found in the immediately above mentioned U.S. patents.

In another assay format, the analyte may occur on or be bound to a larger biological, biochemical or chemical species. This type of format is illustrated by a surface antigen assay. In this format, the specific binding material is capable of specifically binding with the analyte and the presence of analyte is proportional to the analyte-chemiluminescent conjugate complex formed as a reaction product. This is illustrated by attaching the chemiluminescent moiety to an antibody which is specific to a surface antigen on a cell. The presence of the cell surface antigen will be indicated by the chemiluminescence of the cells after the completion of the reaction. The cells themselves may be used in conjunction with a filtration system to separate the analyte-chemiluminescent conjugate complex which is formed on the surface of the cell from unreacted chemiluminescent conjugate. This is discussed further in U.S. Pat. No. 4,652,533.

The improved chemiluminescent moiety may be used in additional assay formats known in the art including without limitation sequential saturation and competitive displacement, both of which utilize a chemiluminescent conjugate where both (1) the specific binding material, to which the moiety is attached, and (2) the analyte specifically bind with a reactant. In the case of sequential saturation, the analyte is reacted with the reactant first, followed by a reaction of the chemiluminescent conjugate with remaining unreacted reactant. In the case of competitive displacement, the chemiluminescent conjugate competitively displaces analyte which has already bound to the reactant.

In a quenching format, the assay utilizes a reactant which is capable of specifically binding with the analyte to form an analyte-reactant complex and with the specific binding material, to which the chemiluminescent moiety is attached, to form a chemiluminescent conjugate-reactant complex. A quenching moiety is attached to the reactant. When brought into close proximity to the chemiluminescent moiety, the quenching moiety reduces or quenches the chemiluminescence of the chemiluminescent moiety. In this quenching format, the presence of analyte is proportional to the chemiluminescence of the chemiluminescent moiety. A further discussion of this format may be found in U.S. Pat. Nos. 4,220,450 and 4,277,437, which are incorporated herein by reference.

In consideration of the above discussed assay formats, and in the formats to be discussed below, the order in which assay reagents are added and reacted may vary widely as is well known in the art. For example, in a sandwich assay, the reactant bound to a solid phase may be reacted with an analyte contained in a sample and after this reaction the solid phase containing complexed analyte may be separated from the remaining sample. After this separation step, the chemiluminescent conjugate may be reacted with the complex on the solid phase. Alternatively, the solid phase, sample and chemiluminescent conjugate may be added together simultaneously and reacted prior to separation. As a still further but less preferred alternative, the analyte in the sample and the chemiluminescent conjugate may be reacted prior to addition of the reactant on the solid phase. Similar variations in the mixing and reaction steps are possible for competitive assay formats as well as other formats known in the art. "Allowing under suitable conditions substantial formation" of specific binding reaction products shall herein include the many different variations on the order of addition and reaction of assay reagents.

In the second category of assay formats, the assay utilizes an unconjugated improved chemiluminescent compound. The presence of analyte in the sample is proportional to the formation of one or more specific binding reaction products which do not themselves contain the chemiluminescent moiety. Instead, the chemiluminescent compound chemiluminesces in proportion to the formation of such reaction products.

In one example of this second category of assays, the assay utilizes a reactant capable of binding with the analyte to form an analyte-reactant complex which causes the chemiluminescent compound to chemiluminesce. This is illustrated by a simple enzyme-substrate assay in which the analyte is the substrate glucose and the reactant is the enzyme glucose oxidase. Formation of the enzyme-substrate complex triggers the chemiluminescent compound. Such enzyme-substrate assay for glucose is disclosed in U.S. Pat. Nos. 3,964,870 and 4,427,770, both of which are incorporated herein by reference. This enzyme-substrate assay is a specific binding assay in the sense that the substrate specifically binds to the active site of the enzyme in much the same way that an antigen binds to an antibody. In this assay, the enzyme specifically binds with the substrate which results in the production of peroxide which, in turn, causes the chemiluminescent compound to chemiluminesce.

Also included in the second category of assays are those assays in which the formation of the reaction products promotes or inhibits chemiluminescence by the chemiluminescent compound in a less direct manner. In this assay, a first reactant, which is cross reactive with the analyte, is attached to an enzyme such as glucose oxidase close to its active site. A second reactant which is specific for both the analyte and the immunoreactive material is added to the sample and the altered enzyme in the presence of the substrate (i.e., glucose). When the second reactant binds to the first reactant located near the active site on the enzyme, the second reactant blocks the active site in a way that the substrate cannot bind to the enzyme at the active site or the binding of the substrate at the active site is significantly decreased. The second reactant blocking the enzyme in this manner inhibits the enzyme from producing peroxide which, in turn, would have triggered the chemiluminescent moiety. Analyte in the sample, however, will tie up the second reactant, thus preventing the second reactant from inhibiting the production of peroxide. The presence of analyte will be proportional to the chemiluminescence of the compound.

The assays contained in the above two categories of assay formats may be heterogeneous or homogeneous. In heterogeneous assays, the reaction products, whose formation is proportional to the presence of analyte in the sample, are separated from other products of the reaction. Separation can be achieved by any means, including without limitation, separation of a liquid phase from a solid phase by filtration, microfiltration, double antibody precipitation, centrifugation, size exclusion chromatography, removal of a solid phase (e.g., a dip stick) from a sample solution or electrophoresis. For example, in a sandwich assay the reactant-analyte-chemiluminescent conjugate complex is separated from unreacted chemiluminescent conjugate. In a surface antigen assay, the analyte-chemiluminescent conjugate complex is separated from unreacted chemiluminescent conjugate. In a competitive assay, the reactant-chemiluminescent conjugate complex is separated from unreacted chemiluminescent conjugate. In a sequential saturation assay and in a competitive displacement assay, the reactant-chemiluminescent conjugate complex is separated from unreacted chemiluminescent conjugate. Alternatively, in homogeneous assays the reaction products are not separated. After the assay reagents have been allowed to react, the chemiluminescence may be measured from the whole assay mixture whether such mixture is in solution, on a solid phase or distributed between various membrane layers of a dip stick or other solid support. The glucose assay using glucose oxidase and a chemiluminescent moiety illustrates a simple homogeneous assay in which separation is unnecessary. The quenching assay illustrates a more complex homogeneous assay in which separation is unnecessary. It is contemplated that either category of assay formats may give rise to either heterogeneous or homogeneous formats.

Finally, "measuring the chemiluminescence" shall include, where relevant, the act of separating those specific binding reaction products, the formation of which are proportional to the presence of analyte in the sample, from other reaction products. It shall also include, where relevant, the acts of triggering the chemiluminescent moiety to chemiluminesce in the case of those assay formats in which the formation of the reaction products does not itself trigger the chemiluminescent moiety.

SYNTHESIS OF MOIETIES

The following examples show the synthesis of certain chemiluminescent moieties of the present invention. These chemiluminescent moieties are typically made in small quantities and the procedures employed for their manufacture do not reflect conventional large scale chemical manufacturing procedures. In these reactions, conventional reactions have been employed to produce the chemiluminescent labels of the invention. Purification procedures suitable for isolating product are conventional laboratory procedures, such as crystallization out of solvent solution by the addition of a nonsolvent, solvent extraction, and the like. In such cases, many different solvents and nonsolvents are suitable. Yields are the amounts recovered as a percentage of reactants employed.

EXAMPLE 1

An illustrative chemiluminescent moiety of the present invention is (2,6-dimethyl-4-nitro)phenyl-3-(3-succinimidyl-oxycarbonyl) propyloxy-N-methyl-acridinium-9-carboxylate fluorosulfonate (or other counter ions such as chloride, trifluoroacetate, sulfate, etc.) which has the following formula:

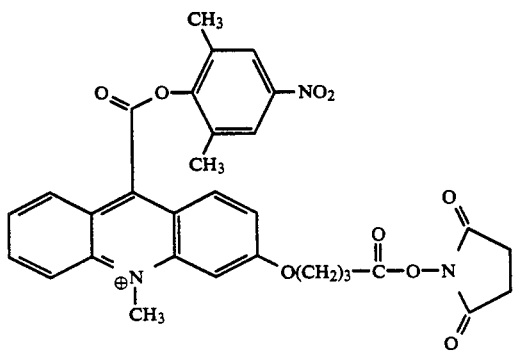

The compound (2,6-dimethyl-4-nitro) phenyl-3-(3-succinimidyl-oxycarbonyl) propyloxy-N-methyl-acridinium-9-carboxylate fluorosulfonate was synthesized according to the following scheme:

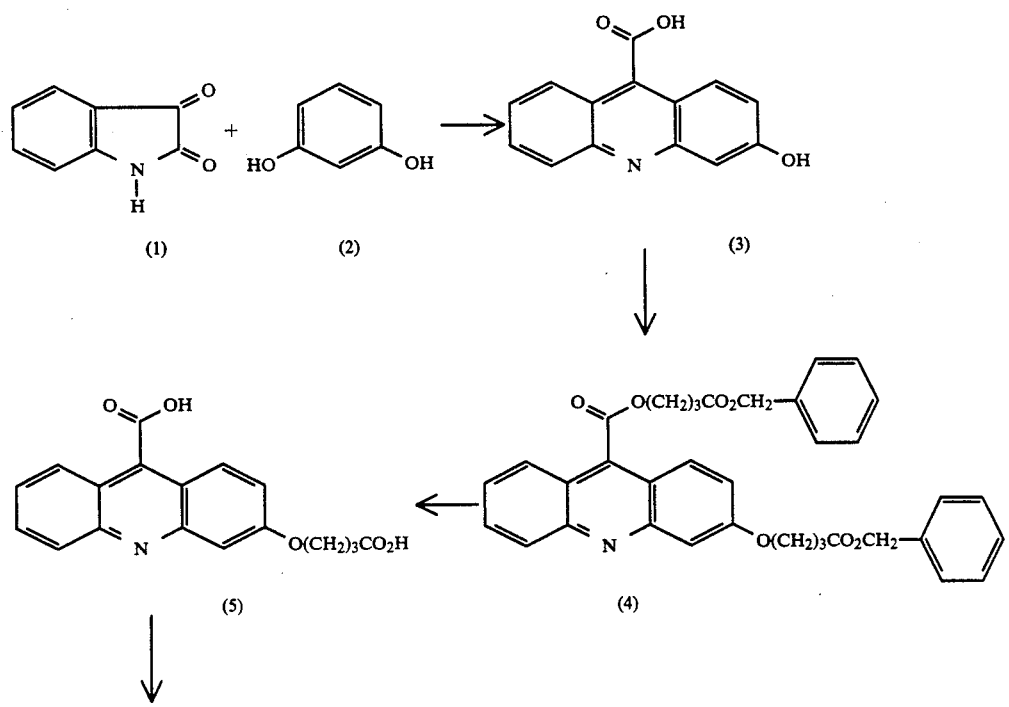

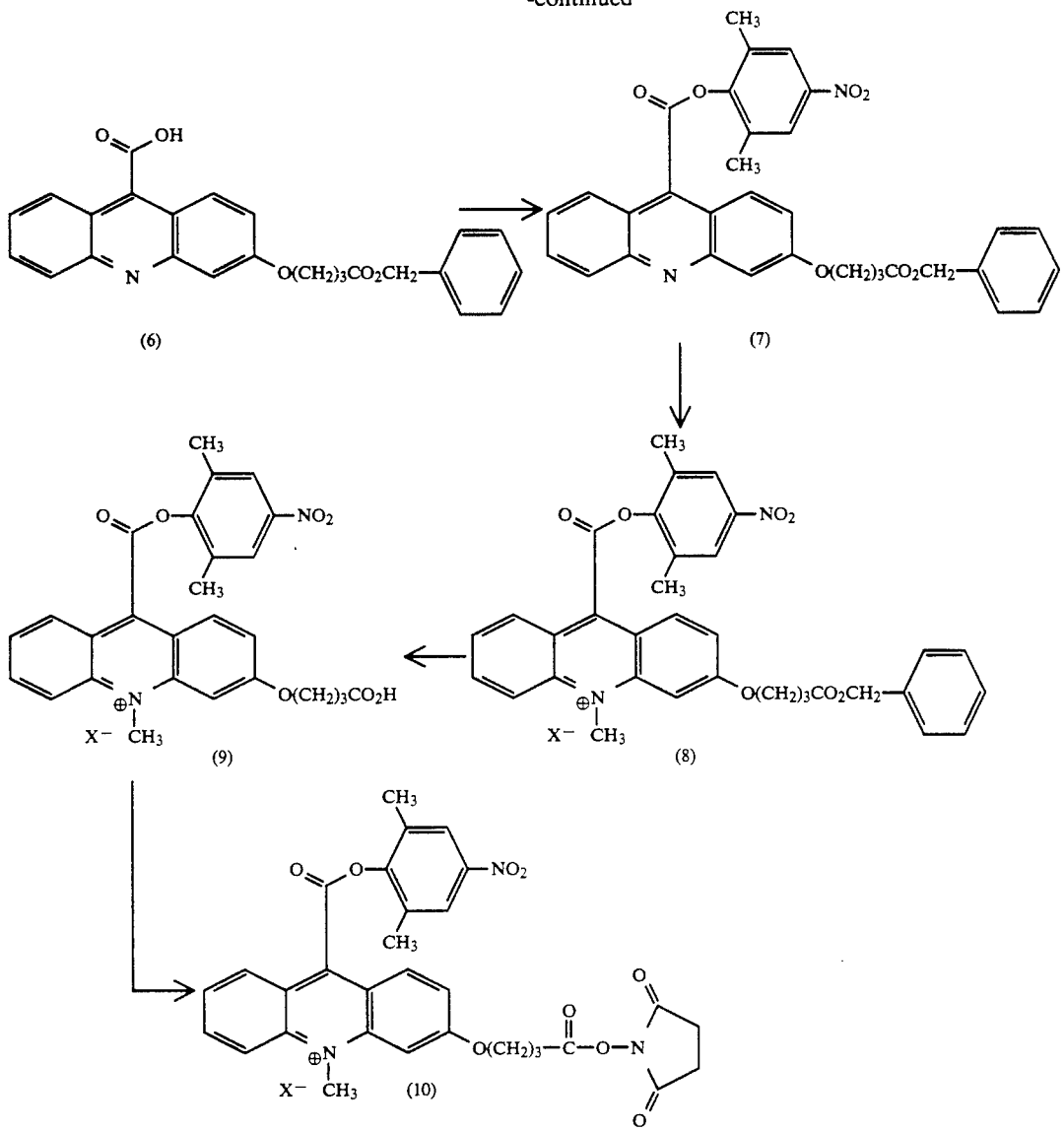

Condensation of isatin (1) with resorcinol (2) provides the 3-hydroxy acridine-9-carboxylic acid (3). Reaction with benzyl-4-bromo butyrate gives the ester (4) with the 3-hydroxy group etherified. Hydrolysis using base removes both the benzyl groups resulting in the dicarboxylic acid (5). Selective rebenzylation of the carboxylic function of the propyloxy group gives 9-carboxylic acid (6). Esterification with 2,6-dimethyl-4-nitrophenol yields (7) and methylation of the acridine nitrogen gives (8). Deprotection of the carboxyl group with HBr provides (9) and condensation with N-hydroxysuccinimide using DCC provides (2,6-dimethyl-4-nitro) phenyl-3-(3-succinimidyl-oxycarbonyl) propyloxy-N-methyl-acridinium-9-carboxylate fluorosulfonate (10). These reactions are described in further detail in the following.

In the first step, 4-bromobutyryl chloride (13.8 g, 75 mmole) was placed in a 100 ml round bottom flask. The flask was cooled to −20° C. using a dry ice/carbon tetrachloride bath. Ethyl acetate (50 ml) containing N-methylmorpholine (7.58 g, 75 mmol, 8.2 ml) was added carefully. Using an addition funnel, benzyl alcohol (6.97 g, 6.67 ml, 6.64 mmoles) was added dropwise. After the addition the bath was removed and the mixture was stirred for 2 hours. The product was transferred to a separatory funnel using ethyl acetate (50 ml), washed once with sodium bicarbonate (10%), then twice with water, and dried with anhydrous sodium sulfate. Evaporation of solvents gave benzyl-4-bromobutyrate as an oil (yield=91%).

Isatin (1) (1.88 g) was slowly added to a solution of potassium hydroxide (5.07 g, 0.09 mole) dissolved in water (3.5 ml). The reaction flask was heated to about 50° C. in an oil bath. About 10 ml more water was added dropwise. Resorcinal (2) (10 g, 0.089 mole) was added and the temperature was raised to 100° C. as stirring was continued, resulting in the formation of a molten mixture. More isatin (1) (1.88 g) was added. The reaction flask (3-necked round bottom) was attached to a nitrogen inlet and the water vapors were flushed out by the stream of nitrogen. The mixture was stirred for 4 hours at 125° C. Water (70 ml) was added and the contents were dissolved by continued stirring. After transferring the mixture to an erlenmeyer flask the volume was brought up to 200 ml with water. The pH was adjusted to 2.0 with concentrated hydrochloric acid. Filtration and washing of the solids with water gave the crude acridine acid. It was then dissolved in 2N NaOH (100 ml) and the solution was filtered through celite. The celite bed was washed with 200 ml of 1N NaOH. The filtrate was acidified with concentrated HCl to pH 2.0. The precipitate of 2-hydroxy-acridine-9-carboxylic acid (3) was filtered, washed with water and was dried in vacuum over $P_2O_5$ (yield=42%).

In the next sequence, 3-hydroxy-9-acridine carboxylic acid (3) (4 g, 0.017 mole), benzyl-4-bromobutyrate (14.6 g, 0.057 mole) and cesium carbonate (22.16 g, 0.068 mole) were dissolved in DMSO (125 ml) in a 250 ml round bottom flask. The flask was warmed to about 50° C. in an oil bath. After stirring the mixture at that temperature for 1 hour, the mixture was poured into water (1 liter). The precipitated product was extracted with chloroform after making the aqueous suspension basic with sodium bicarbonate. Drying and evaporation of chloroform gave 3-(3-benzyloxycarbonyl)-propyloxy-9-(3-benzyloxy-carbonyl-propyl) acridine carboxylate (4) which was chromatographed on a silica gel column using chloroform as solvent. Fractions with $R_f$ value of 0.36 on TLC with $CHCl_3$/EtOAc, 9/1, were pooled. The solvents were evaporated (yield=55%).

Then, 3-(3-benzyloxycarbonyl)-propyloxy-9-(3-benzyloxycarbonyl propyl) acridine carboxylate (4) (4.93 g, 8.3 mmole) was added to a mixture of 2N NaOH (300 ml) and methanol (300 ml). The mixture was stirred at room temperature for 48 hours. The methanol was removed on a rotary evaporator and the solution was acidified with concentrated hydrochloric acid to pH 6.0. The precipitated solids were filtered, washed with water and dissolved in ethyl acetate. The solution was dried and then the solvents were evaporated to give 3-(3-carboxy)propyloxy-acridine-9-carboxylic acid (5) (yield=92.8%).

This compound, 3-(3-carboxy)propyloxy-acridine-9-carboxylic acid (5) (1.5 g, 4.6 mmole), was dissolved in DMAP (80 ml, 1,3-dimethyl-3,4,5,6-tetrahydro-2(1H)-pyrimidone) with warming. Benzyl alcohol (0.5 ml, 0.52 g, 4.8 mmole), 1,3-dicyclohexylcarbodiimide (1.04 g, 5.0 mmole) and N,N-dimethyl aminopyridine (0.2 g, 1.6 mmole) were added to the reaction which was previously cooled in a bath of dry ice/$CCl_4$. The mixture was stirred for 15 hours with a nitrogen inlet at room temperature. The mixture was added to saturated sodium chloride (320 ml). 3-(3-benzyloxycarbonyl)propyloxyacridine-9-carboxylic acid (6) was filtered and was washed with a small amount of water. The product was chromatographed on a silica gel column using $CHCl_3$/MeOH, 95/5 as solvent (yield=26%).

The compound 3-(3-benzyloxycarbonyl)propyloxy-acridine-9-carboxylic acid (6) (0.5 g, 1.2 mmole) and p-toluene sulfonyl chloride (0.46 g, 2.4 mmole) were dissolved in pyridine (20 ml). The solution was cooled in a bath of dry ice/$CCl_4$ for 15 minutes. 2,6-dimethyl-4-nitrophenol (0.2 gm, 1.2 mmole) was added and the cooling bath was removed and the mixture was stirred for 15 hours at room temperature. It was added to water (450 ml) and the pH was adjusted to 2.0 with concentrated hydrochloric acid. The product was filtered, washed with water and was dried in vacuum. The crude product was chromatographed on a silica gel column using chloroform as solvent. Fractions with an $R_f$ value of 0.8 on TLC with $CHCl_3$/EtOAc, 1:1, were pooled. Evaporation of solvents gave (2,6-dimethyl-4-nitro)-phenyl-3-(3-benzyloxycarbonyl)-propyloxy-acridine-9-carboxylate (7) (yield=47%).

The acridine (7) (0.32 g, 0.56 mmole) was dissolved in anhydrous methylene chloride (4 ml) and methyl fluorosulfate (0.27 ml, 3.36 mmole, 6 molar equivalent) was added. The mixture was stirred for 15 hours at room temperature. Anhydrous ether (20 ml) was added. (2,6-dimethyl-4-nitro)phenyl-3-(3-benzyloxycarbonyl)-propyloxy-acridinium-9-carboxylate fluorosulfonate (8) was filtered and washed with ether (50 ml). The yield was quantitative.

The benzyl-protected acridinium ester (8) (250 ng) was treated with 30% HBr/Acetic acid (3 ml) for 2 hours at 55° C. Anhydrous ether (20 ml) was added to precipitate the product. Filtration and washing of the solids with ether gave (2,6-dimethyl-4-nitro)phenyl-3-(3-carboxyl)propyloxy-acridinium-9-carboxylate fluorosulfonate (9). Crystallization from acetonitrile provided the pure compound (yield=80%). Purification by crystallization from other solvents achieves equivalent results. The same results may be achieved by crystallization from acetonitrile by the addition of ethyl acetate. Other useful solvent combinations include alcohol and ether, such as methanol, ethanol or propanol and diethyl ether (ether is the precipitating solvent).

The deprotected acridinium (9) (67 mg, 0.13 mmole) in a 50 ml 2-necked round bottom flask was dissolved in anhydrous acetonitrile (10 ml). Dicyclohexylcarbodiimide (DCC, 33 mg, 0.16 mmole) was added and the mixture stirred for 45 minutes at room temperature. N-hydroxysuccinimide (17 mg, 0.15 mmole) was added and reaction continued for 2.5 hours. More DCC (14 mg) and N-hydroxysuccinimide (8 mg) were added and followed again by the same amounts after 1.5 hours. After 1.5 hours after the last addition, glacial acetic acid (1.7 ml) was added to quench excess DCC. The solvent was removed in vacuo.

The crude product was purified on a semi-preparative $C_{18}$-Dynamax HPLC column (commercially available from Rainin Instrument Co., Inc., Woburn, Mass.) using $CH_3CN$/$H_2O$ (0.1% Trifluoroacetic acid) 60/40, as the mobile phase at a flow rate of 1.8 ml/min, using 360 nm for detection. The fraction at retention time 9.4 minutes was collected and the solvents were removed in vacuo. The (2,6-dimethyl-4-nitro)-phenyl-3-(3-succinimidyl-oxycarbonyl) propyloxy-acridinium-9-carboxylate fluorosulfonate (10) was dried under vacuum in a dessicator containing phosphorus pentoxide (yield=33%). MS:FAB, thioglycerol matrix, 586 (M+). HPLC: Rainin $C_{18}$ Dynamax (10 mm×25 mm), $CH_3CN$/$H_2O$ (0.1% trifluoracetic acid), 60:40, flow rate 1.8 ml/min, retention time 9.4 min, detected at 360 nm.

EXAMPLE 2

Another chemiluminescent label the present invention is (2,6-dimethoxy-3-chlorosulfonyl)phenyl-N-methyl-acridinium-9-carboxylate fluorosulfonate which has the following formula:

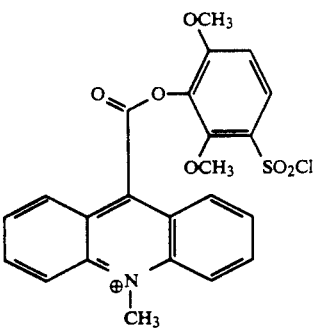

This compound, (2,6-dimethoxy-3-chlorosulfonyl)phenyl-N-methyl-acridinium-9-carboxylate fluorosulfonate, was synthesized according to the following scheme:

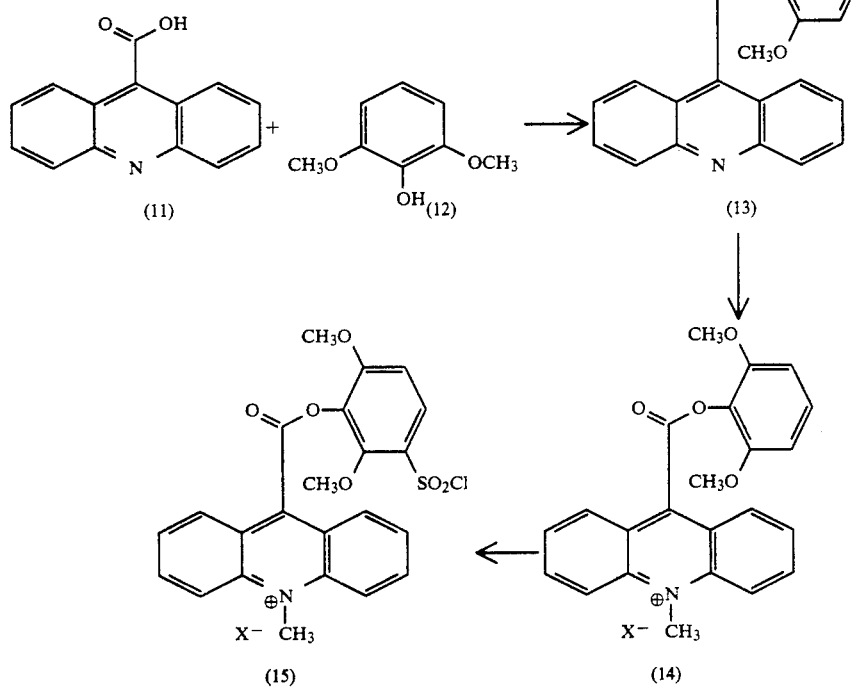

Esterification of acridine-9-carboxylic acid (11) with 2,6-dimethoxyphenol (12) via the acid chloride (not shown) provides the ester (13). Methylation of the acridine nitrogen with methylfluorosulfate (14) and subsequent chlorosulfonation with chlorosulfonic acid gives the label (15). These reactions are described in further detail in the following.

Acridine-9-carboxylic acid (11) (6.10 g, 0.027 moles) in a 250 ml round bottom flask was mixed with thionyl chloride (130 ml) and the mixture was refluxed for 2 hours with stirring. The excess thionyl chloride was removed in a rotary evaporator. The residue was treated with benzene (75 ml) and the solvent was removed in vacuo to remove traces of thionyl chloride. The residue of acridine-9-carbonyl chloride (11) was mixed with pyridine (130 ml) and 2,6-dimethoxyphenol (12) (4.16 g, 0.027 moles) was added. The mixture was warmed using a water bath (about 60° C.) to dissolve all the solids. After 15 hours of stirring at room temperature the mixture was poured into 1 liter of water. The suspension was acidified with concentrated hydrochloric acid to pH 2.0. The solid product was filtered, washed with water and dissolved in chloroform. Drying (anhydrous sodium sulfate) and evaporation of chloroform gave (2,6-dimethoxy)phenyl-acridine-9-carboxylate (13). This was chromatographed on a silica gel column using CHCl₃/EtOAc, 98:2 as solvent. The fractions with $R_f$ value of 0.19 on TLC with the same solvent were pooled and evaporation of the solvents gave the pure ester (13) (yield=30%). Esterification may also be effected with the procedure of Brewster et al., *J. Am. Chem. Soc.*, 77, 6214–6215 (1955), hereinafter called Brewster.

The compound (2,6-dimethoxy)phenyl-acridine-9-carboxylate (13) (2.01 g, 5.6 mmole) was dissolved in dichloromethane (110 ml, anhydrous) in a 250 ml round bottom flask. Methyl fluorosulfate (4.60 ml, 6.48 g, 56 mmoles) was added and the mixture was stirred at room temperature for 15 hours. Anhydrous ether (100 ml) was added and the precipitated bright yellow solids were filtered after stirring the suspension for 0.5 hours. The solid was washed well with ether (about 100 ml) and then with pentane (50 ml). The acridinium was recrystallized from acetonitrile to provide pure 2,6-dimethoxy-phenyl-acridinium-9-carboxylate fluorosulfonate (14) (yield=81%). The same results may be achieved by crystallization from acetonitrile by the addition of ethyl acetate. Other useful solvent combinations include alcohol and ether, such as methanol, ethanol or propanol and diethyl ether (ether is the precipitating solvent).

In a dry two neck 25 ml round bottom flask were placed the (2,6-dimethoxy)phenyl-10-methyl acridinium-9-carboxylate fluoro-sulfonate (14) (101.7 mg, 0.215 mmole), a magnetic stirring bar and anhydrous CH₂Cl (5 ml). The suspension was stirred and cooled to −20° C. in a CCl₄/dry ice bath. Chlorosulfonic acid (72 μl, 0.125 g, 1.07 mmole) was added and stirring continued at −20° C. for 30 minutes. The reaction mixture was then allowed to warm slowly to room temperature and stirred for an additional 2 hours. Anhydrous ether (5 ml) was added to the reaction flask causing the formation of a light yellow precipitate. It was filtered and washed thoroughly with ether. Drying under vacuum gave (2,6-dimethoxy-3-chlorosulfonyl)phenyl acridinium-9-carboxylate fluorosulfonate (15) (yield=93.4%). MS:FAB, dithiothreitol/dithioerythrytol matrix, 472 (M+).

A modification of this procedure, the chlorosulfonyl content of the compound (15) can be increased (see March, *Advanced Organic Chemistry*, John Wiley & Sons, p. 445 (1985)) by single or multiple treatments with thionyl chloride, phosphorus pentachloride, and the like, in the manner indicated above with respect to forming carboxylic acid chloride. However, the chlorosulfonyl content of the compound is not critical to its use as a label in view of the fact that many molar excess of the label is used in making a conjugate, typically exceeding the stoichiometry for chlorosulfonyl to complementary group, viz., lysine amino group, present in the specific binding material. The resulting conjugate is desirably purified to 100% purity prior to usage.

EXAMPLE 3

Another chemiluminescent label of the present invention is (2,6-dimethyl-4-bromo)phenyl-N-methyl-acridinium-9-carboxylate fluorosulfonate which has the following formula:

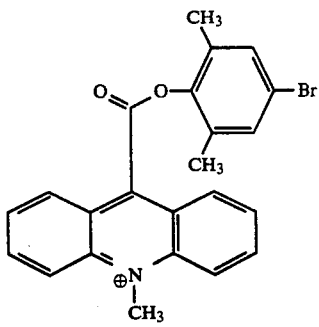

The compound 9-(2,6-dimethyl-4-bromo)phenyl-N-methyl-acridinium-9-carboxylate fluorosulfonate was synthesized by the same esterification procedure as (2,6-dimethoxy-3-chlorosulfonyl)phenyl-N-methyl-acridinium-9-carboxylate fluorosulfonate, with the substitution of 2,6-dimethyl-4-bromo-phenol for the substituted phenol employed in the (2,6-dimethoxy-3-chlorosulfonyl)phenyl-N-methyl-acridinium-9-carboxylate fluorosulfonate synthesis.

EXAMPLE 4

Another chemiluminescent label of the present invention is (2,6-dimethyl-3-chlorosulfonyl)phenyl-N-methyl-acridinium-9-carboxylate fluorosulfonate which has the following formula:

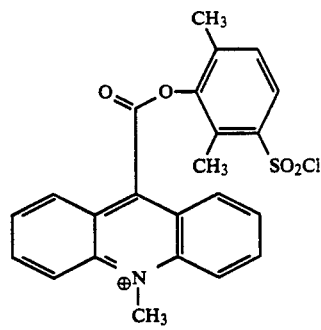

The compound (2,6-dimethyl-3-chlorosulfonyl)phenyl-N-methyl-acridinium-9-carboxylate fluorosulfonate was synthesized by the same method as (2,6-dimethoxy-3-chlorosulfonyl)phenyl-N-methyl-acridinium-9-carboxylate fluorosulfonate with the substitution of 2,6-dimethylphenol for 2,6-dimethoxyphenol in the esterification step.

EXAMPLE 5

Further illustrative of the present invention is (2,6-dimethyl-4-nitro)phenyl-3-(3-succinimidyloxycarbonyl)propyloxy-9,10-dihydro-N-methyl-acridan-9-carboxylate which has the following formula:

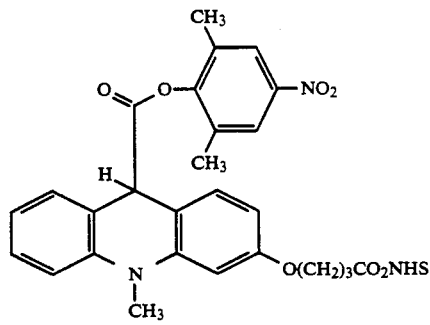

The compound (2,6-dimethyl-4-nitro)phenyl-3-(3-succinimidyloxycarbonyl) propyloxy-9,10-dihydro-N-methyl-acridan-9-carboxylate was synthesized from the acridinium acid (9). Reduction of the acid (9) with sodium cyanoborohydride gives the acridan which is then converted to the NHS ester by the mixed anhydride method. These reactions are described in further detail in the following.

The acridinium acid (9) (210 mg, 0.37 mmole) was dissolved in a 1:1 mixture of acetonitrile and 0.1M phosphate buffer, pH 5.2 (60 ml). A solution of sodium cyanoborohydride (190 mg) in acetonitrile (5 ml) was added dropwise to the acridinium solution. This results in the bleaching of the yellow color of the solution. Stirring was continued for 15 minutes. Acetonitrile (100 ml) was added and the solvents were removed in a rotary evaporator. The residue as a suspension in water is extracted with ethylacetate. The organic layer was washed with water and dried. Removal of solvents gave (2,6-dimethyl-4-nitro)phenyl-3-(3-carboxyl)propyloxy-9,10-dihydro-acridan-9-carboxylate (yield=90%).

The acridan acid (125 mg, 0.255 mmole) and N-methylmorpholine (28 l) were dissolved in anhydrous acetonitrile (15 ml). The mixture was cooled in a CCl₄/dry ice bath under nitrogen. Isobutylchloroformate (35 μl) was added, the mixture was stirred for 3 minutes and N-hydroxysuccinimide (35 mg) dissolved in acetonitrile (2 ml) was added. After stirring at −20° C. for 15 minutes the CCl4/dry ice bath was removed and the reaction allowed to warm up to room temperature. After 2 hours the solvents were evaporated and the residue extracted into ethyl acetate. The insoluble N-methylmorpholine hydrochloride salt was removed by filtration. The filtrate was concentrated and hexane (20 ml) was added. Cooling results in crystallization of (2,6-dimethyl-4-nitro)phenyl-3-(3-succinimidyloxy-carbonyl) propyloxy-9,10-dihydro-N-methyl-acridan-9-carboxylate. The crystals were finally filtered and washed with hexane (yield=70%). MS: FAB, dithiothreitol/dithioerythrytol matrix, 588 (M+ +1). HPLC: Waters C$_{18}$ Novapak (3.9 mm×15 mm) (commercially available from Millipore Corporation, Waters Chromatography Division, Milford, Mass.), CH$_3$CN/H$_2$O (0.1% trifluoracetic acid) 60:40, flow rate 1.0 ml/min, retention time 6.34 min, detected at 280 nm.

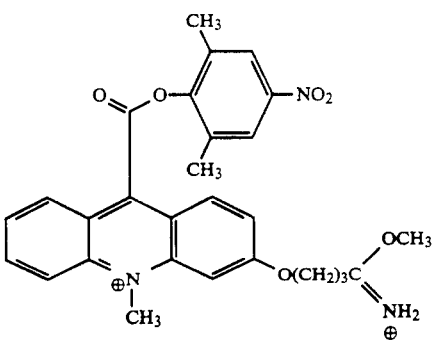

The compound (2,6-dimethyl-4-nitro)phenyl-N-methyl-acridinium-9-carboxylate-3-oxo-butyrimidate chloride, hydrochloride is synthesized according to the following scheme:

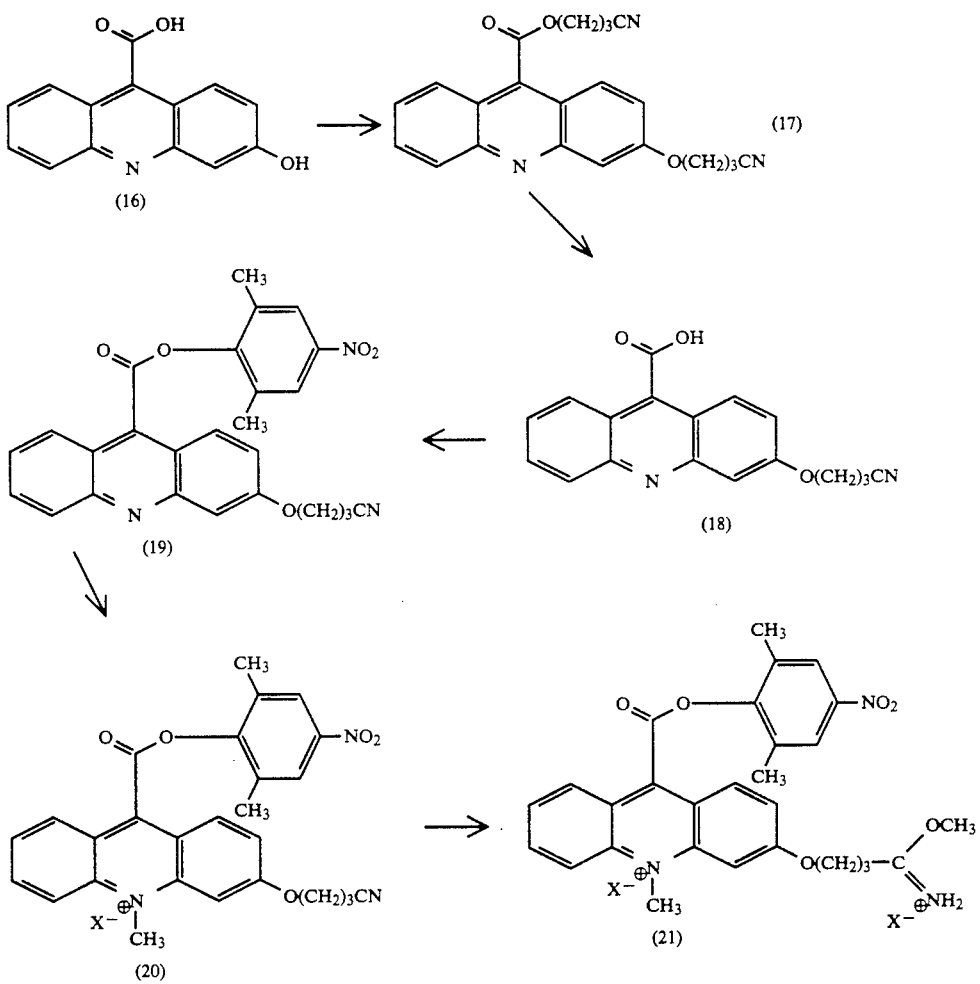

EXAMPLE 6

Another structure encompassed by the invention is (2,6-dimethyl-4-nitro) phenyl-N-methyl-acridinium-9-carboxylate-3-oxo-butyrimidate chloride, hydrochloride which has the following formula:

Reaction of 3-hydroxy-9-acridine carboxylic acid (16) with 4-bromobutyronitrile gives an ester (17). Hydrolysis of the ester and reesterification with 2,6-dimethyl-4-nitrophenol provides (19). Methylation with methyl fluorosulfate and conversion of the cyano group to the imidate ester using hydrogen chloride gas and methanol provides (2,6-dimethyl-4-nitro)phenyl-N-methyl-acridinium-9-carboxylate-3-oxo-butyrimidate chloride, hydrochloride (21). These reaction are described in further detail in the following.

In this reaction, 3-hydroxy-9-acridine carboxylic acid (16) (2 g, 8.4 mmole), 4-bromobutyronitrile (5.87 ml, 8.74 g, 34 mmole) and cesium carbonate (11.08 g, 34 mmole) were dissolved in anhydrous DMSO (50 ml) in a 100 ml round bottom flask. The mixture was warmed to about 50° C. in a water bath with stirring. After 3 hours the mixture was poured into water (600 ml). The solids were filtered and were dissolved in chloroform. Drying and evaporation of the solvent gave 3-(3-cyano) propoxyl-acridine-9-carboxylic acid-(3-cyano)propyl ester (17). It was then dissolved in toluene (50 ml) and cyclohexane (150 ml) was added. The pure product (17) separated, and was then filtered and dried. The dried product was purified by thin layer chromatography with ethylacetate as the mobile phase ($R_f$=0.58) (yield=78.6%).

The cyanopropyl ester (17) (3.73 g. 10 mmoles) was dissolved in a mixture of 0.5N NaOH (90 ml) and methanol (90 ml) and stirred in a water bath at 60° C. using a reflux condenser for 2.5 hours. The methanol was removed in a rotary evaporator and the product was extracted with ethyl acetate after acidifying the aqueous phase with concentrated hydrochloric acid. Drying and evaporation of the solvent provides 3-(3-cyano) propoxyl-acridine-9-carboxylic acid (18) (yield=80%).

The carboxylic acid (18) (4.62 g, 15 mmole) was dissolved in pyridine (130 ml) and the solution was cooled in a CCl4/dry ice bath. Para toluenesulfonyl chloride (5.8 g, 30 mmole) was added and the bath was removed. After 15 minutes of stirring at room temperature, 2,6-dimethyl-4-nitrophenol (2.8 g, 16.8 mmole) was added. After 18 hours at room temperature, water (10 ml) was added and the solvents were removed in vacuo. The residue was dissolved in chloroform (200 ml) and the organic layer was washed with saturated sodium bicarbonate (2×100 ml), water (2×100 ml), 1N HCl (1×100 ml) and finally with water (2×100 ml). Drying and evaporation of the solvent gave (2,6-dimethyl-4-nitro)-phenyl-3-(3-cyano) propoxyl-acridine-9-carboxylate (19) which was chromatographed in a silica gel column using ethylacetate/hexane (7:3) as solvent (yield=74.5%).

The ester (19) (1.6 g, 3.52 mmole) was dissolved in dry methylene chloride (50 ml) and under nitrogen methyl fluorosulfate (1.6 ml, 17.6 mmole) was added. The solution was stirred at room temperature for 20 hours. Anhydrous ether (100 ml) was added and the precipitated (2,6-dimethyl-4-nitro)phenyl-3-(3-cyano) propoxyl-acridinium-9-carboxylate fluorosulfonate (20) was filtered, washed with ether and dried in vacuo (yield=84.7%).

The acridinium ester (20) (4 mg, 7.4×10$^{-3}$ mmole) was dissolved in methanol (0.5 ml) in a 5 ml 2-necked flask. Anhydrous hydrogen chloride gas was bubbled carefully for 10 minutes. Anhydrous ether (3 ml) was added. The precipitated (2,6-dimethyl-4-nitro)phenyl-N-methyl-acridinium-9-carboxylate-3-oxo-butyrimidate chloride, hydrochloride (21) was collected and washed with ether. The solid was dried in vacuum and was stored in a dessicator containing phosphorus pentoxide.

EXAMPLE 7

Another chemiluminescent label of the present invention is (2,6-dimethyl-4-nitro)phenyl-N-methyl-phenanthridinium-6-carboxylate fluorosulfonate which has the following formula:

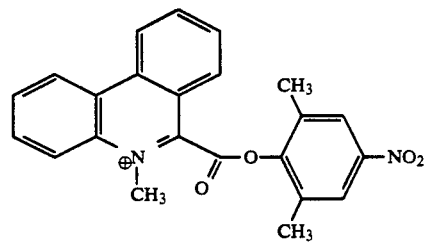

The compound (2,6-dimethyl-4-nitro)phenyl-N-methyl-phenanthridinium-6-carboxylate fluorosulfonate is synthesized according to the following scheme:

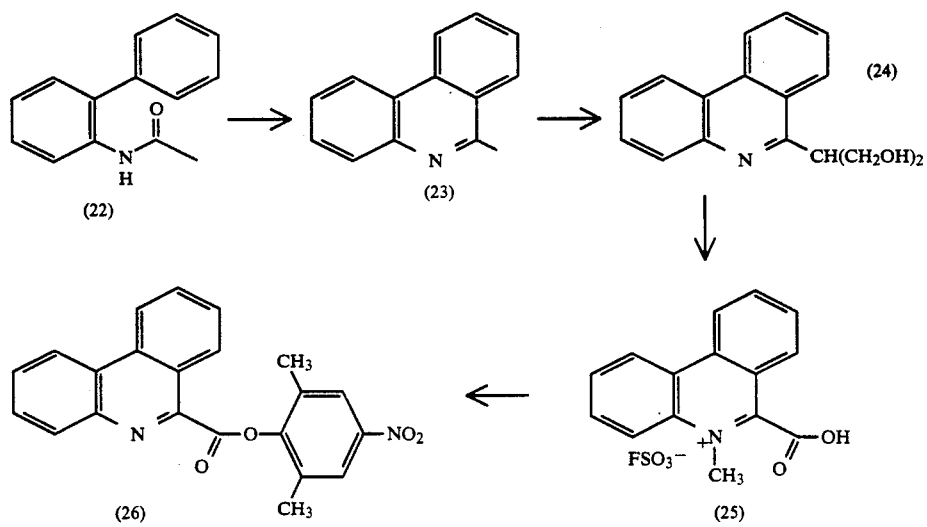

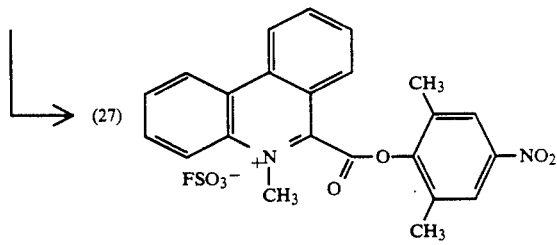

In the reaction, 2-aminobiphenyl (16.9 g, 0.1 mol) is dissolved in anhydrous pyridine (30 ml) and acetic anhydride (10.5 ml, 0.11 mol) added to the solution. The solution is shaken briefly and cooled to room temperature and let stand for 15 hours. After the addition of water (50 ml) N-acetyl-2-aminobiphenyl (22) is filtered off and recrystallized from aqueous ethanol to give 19.6 g of white needles (yield=93%).

Then N-acetyl-2-aminobiphenyl (22) (19 g, 0.09 mol) is gently refluxed with freshly distilled phosphoryl chloride (45 ml, 0.49 mol) for 80 minutes. The solution is then cooled in ice and the precipitate (6-methyl-phenanthridine-hydrochloride) filtered off, dissolved in water and made alkaline with aqueous ammonia. The solution is then extracted with ether (4×75 ml). The extract is dried over sodium sulfate and the ether is removed in vacuo. The resulting yellow oil dissolves in boiling cyclohexane (400 ml) and on cooling forms white needles of 6-methylphenanthridine (23) (yield=63%).

The compound 6-(2-hydroxy-1-hydroxymethylethyl)-phenanthridine (24) may be prepared by treating 6-methylphenanthridine (23) with formaldehyde according to the method of Morgan and Walls, J. Chem. Soc. 34:2447 (1931), which is incorporated herein by reference. The compound 6-(2-hydroxy-1-hydroxymethylethyl)-phenanthridine (24) is formed as white needles (yield=57%).

In the next step, a mixture of 6-(2-hydroxy-1-hydroxymethyl)-phenanthridine (24) (6 g, 31 mmoles) and finely powdered selenium dioxide (3.8 g, 34 mmoles) is refluxed in ethyl acetate (125 ml) for 10 hours. The deep red solution that form is then filtered while hot through celite, before evaporating to dryness. The resulting solid is digested in warm 1M hydrochloric acid (125 ml), filtered and partially neutralized with sodium bicarbonate. The initial red precipitate is filtered off before completely neutralizing the solution. The resulting pale yellow solid is filtered off and recrystallized from acetone/petroleum ether to give 2.7 g of 6-formylphenanthridine (yield=42%).

The compound 6-carboxyphenanthridine (25) is prepared by chromic acid oxidation of 6-formylphenanthridine according to the method of Morgan and Walls, J. Chem. Soc., supra. The product (25) is a white powder (yield=60%).

In the next step of the procedure, 6-carboxyphenanthridine (25) (662 mg, 3 mmoles) is dissolved in anhydrous pyridine (14 ml) and cooled to 0° C. Para-toluenesulfonyl chloride (1.15 g, 6 mmoles) is added followed by 2,6-dimethyl-4-nitro-phenol (501 mg, 3 mmoles) and the mixture is allowed to stand overnight at 4° C. The resulting brown solution is stirred into iced water. The precipitate, filtered off, was chromatographed on a silica gel using chloroform/hexane (1:1) to obtain (2,6-dimethyl-4-nitro)phenyl-phenanthridine-6-carboxylate (26) (yield=60%).

In a dry two neck 25 ml round bottom flask the ester (26) (369 mg, 1 mmole) is suspended in anhydrous methylene chloride (5 ml). The suspension is cooled in a dry ice/CCl$_4$ bath under nitrogen. Chlorosulfonic acid (342 ml, 6 mmole) is added and stirring continued at −20° C. for 30 minutes. The mixture, after warming slowly to room temperature, was stirred for an additional 2 hours. Anhydrous ether (20 ml) is added and the precipitated solids filtered and washed with ether. Drying gives (2,6-dimethyl-4-nitro)phenyl-N-methyl-phenanthridinium-6-carboxylate fluorosulfonate (27) (yield=90%).

EXAMPLE 8

The compound (2,6-dimethoxy-3-chlorosulfonyl-phenyl)-2-phenyl-N-methyl-quinolinium-4-carboxylate fluorosulfonate, which has the following formula:

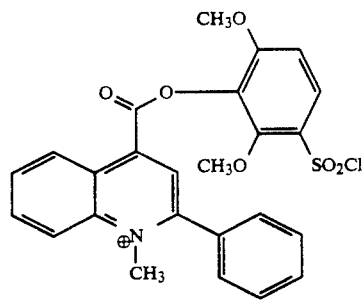

is synthesizable according to the following scheme:

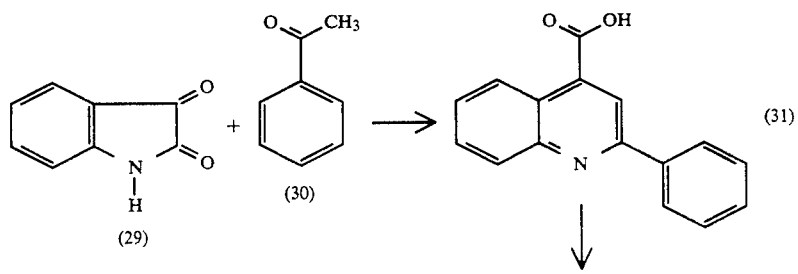

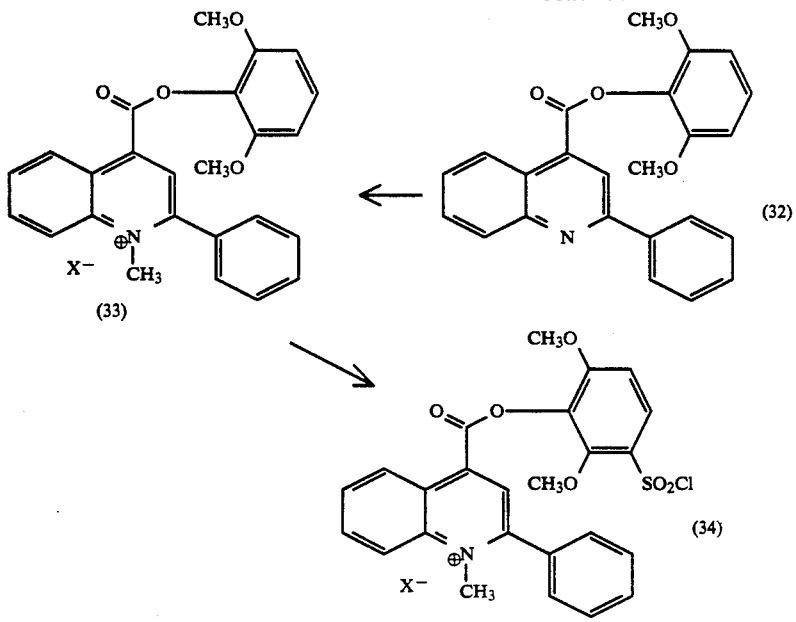

Acetophenone (29) (120 g, 1 mol) and isatin (30) (147 g, 1 mol) would be refluxed for 10 hours in water and ethanol, with potassium hydroxide (17 g). The 2-phenyl-quinoline-4-carboxylic acid (31) is recovered from ethanol as white needles.

The 2-phenyl-quinoline carboxylic acid (31) (735 mg, 3 mmoles) is dissolved in anhydrous pyridine (14 ml) and cooled in an icewater bath. Para-toluene sulfonyl chloride (1.15 g, 6 mmoles) is added and the mixture stirred for 15 mins. Then 2,6-dimethoxy phenol (462 mg, 3 mmoles) is added and the mixture stirred at room temperature for 15 hours. The solution is poured into ice water (300 ml) and the (2,6-dimethoxy)phenyl-2-phenyl-quinoline-4-carboxylate (32) would be filtered. The solids are dried and purified on a silica gel column using chloroform/hexane (1:1).

Methyl fluorosulfate (492 µl, 0.69 g, 6 mmoles) is added to the ester (32) (381 g, 1 mmole) dissolved in anhydrous methylene chloride (3 ml). After stirring for 15 hours at room temperature under nitrogen, anhydrous ether (20 ml) is added. The (2,6-dimethoxy)phenyl-2-phenyl-quinoline-4-carboxylate-N-methylate (33) is filtered and washed with ether and dried.

The ester (33) (200 mg, 0.4 mmole) was suspended in anhydrous methylene chloride (5 ml) and cooled in a dry ice/CCl$_4$ bath under nitrogen in a dry two neck 25 ml round bottom flask. Chlorosulfonic acid (144 µl, 2 mmole) is added and stirring continued at $-20°$ C. for 0.5 hours. The mixture is then allowed to warm slowly to room temperature and stirred for an additional 2 hours. Anhydrous ether (20 ml) is added and the precipitated (2,6-dimethoxy-3-chlorosulfonyl)phenyl-2-phenyl-N-methyl-quinolinium-4-carboxylate fluorosulfonate (34) filtered and washed with ether and dried.

EXAMPLE 9

The compound (2,6-dimethyl-4-trimethylammonio)phenyl-N-methyl-acridinium-9-carboxylate difluorosulfonate has the following formula:

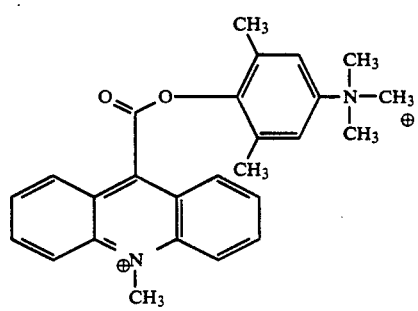

This compound, (2,6-dimethyl-4-trimethylammonio)-phenyl-N-methyl-acridinium-9-carboxylate difluorosulfonate, was synthesized according to the following scheme:

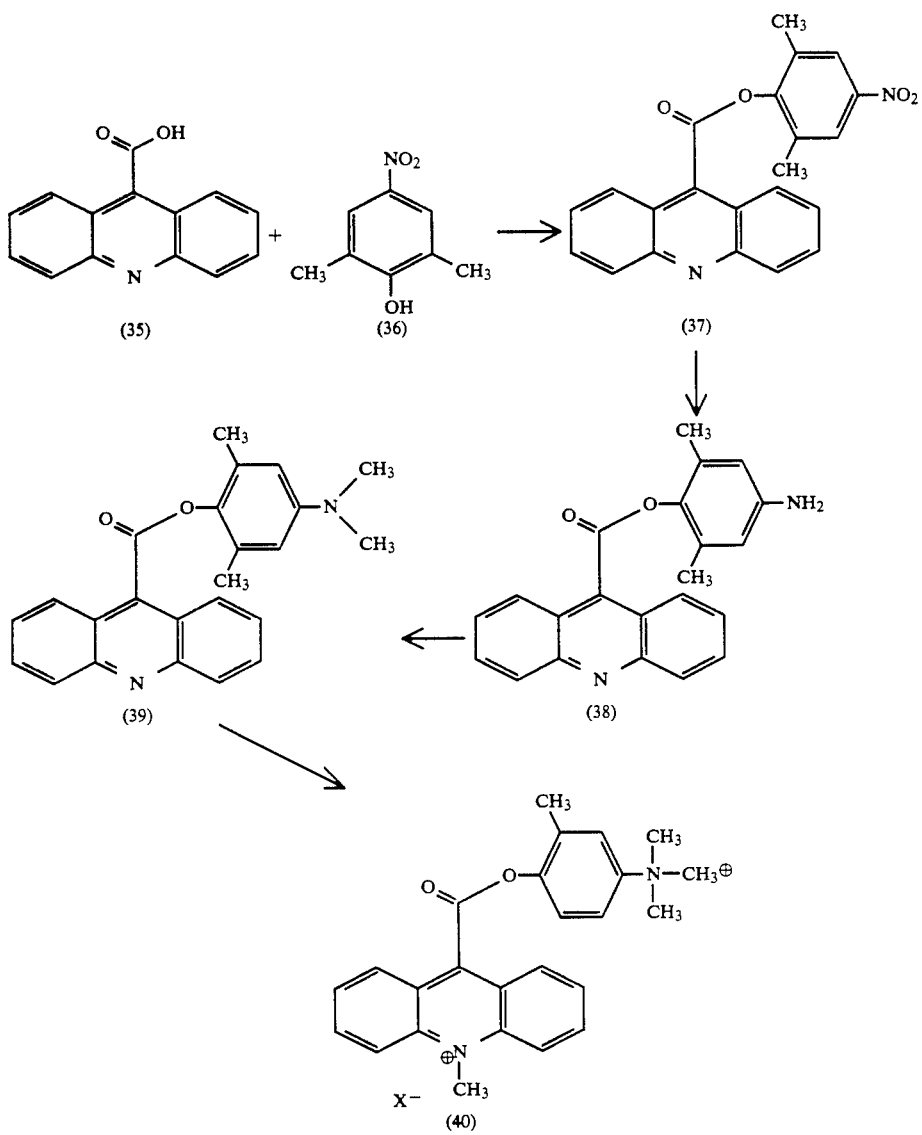

In the reaction scheme, (2,6-dimethyl-4-trimethylammonio)phenyl-N-methyl-acridinium-9-carboxylate (40) was obtained by esterification of acridine-9-carboxylic acid (35) with 2,6-dimethyl-4-nitrophenol (36). The product (37) was reduced to the (2,6-dimethyl-4-amino)phenyl-acridine-9-carboxylate (38) with zinc. Two methyl groups were introduced on the amino group by treatment with methyl iodide. Quaternization and acridinium formation was then accomplished using methyl fluorosulfate. These reactions are described in further detail in the following.

Acridine-9-carboxylic acid (35) (3.05 g, 0.014 moles) in a 250 ml round bottom flask was mixed with thionyl chloride (65 ml) and the mixture was refluxed for 2 hours with stirring. The excess thionyl chloride was removed in a rotary evaporator. The residue was treated with benzene (75 ml) and the solvent was removed in vacuo to remove traces of thionyl chloride. The residue of acridine-9-carbonyl chloride was mixed with pyridine (65 ml) and 2,6-dimethyl-4-nitrophenol (36) (2.25 g, 0.014 moles) was added. The mixture was warmed using a water bath (about 60° C.) to dissolve all the solids. After 15 hours of stirring at room temperature the mixture was poured into 1 liter of water. The suspension was acidified with concentrated hydrochloric acid to pH 2.0. The solid product was filtered, washed with water and dissolved in chloroform. Drying (anhydrous sodium sulfate) and evaporation of chloroform gave the crude ester.

The crude ester was chromatographed on a silica gel column using $CHCl_3/EtOAc$ 98:2 as solvent. The fractions with $R_f$ value of 0.6 on TLC with the same solvent were pooled and evaporation of the solvents gave pure (2,6-dimethyl-4-nitro)phenyl-acridine-9-carboxylate (37) (yield = 30%).

The (2,6-dimethyl-4-nitro)phenyl ester (37) (1.16 g, 3.1 mmole) was dissolved in acetic acid (50 ml) by warming in an oil bath at about 65° C. Stannous chloride (1.5 g) was dissolved in concentrated hydrochloric acid (10 ml) and was added to the ester solution. The mixture was stirred for 45 minutes and was then poured into water (750 ml). Extraction with chloroform (3×200 ml) removed unreacted (2,6-dimethyl-4-nitro)-phenyl ester. The aqueous layer was made basic with sodium bicarbonate and was extracted with chloroform (4×200 ml). Drying and evaporation of the chloroform gave (2,6-dimethyl-4-amino)phenyl-acridine-9-carboxylate (38) (yield=25%).

The amino ester (38) (64 mg, 0.18 mmole) was dissolved in nitromethane (5 ml). Methyl iodide (1 ml) and pyridine (0.1 ml) were added. The mixture was stirred at room temperature for 15 hours. Methanol (2 ml) was added and the mixture was then stirred for an additional 2 hours. The solvents were evaporated and the residue was treated with water (10 ml) and was then extracted with chlroform (4×20 ml) after the solution was made basic. Drying and evaporation of the chloroform gave (2,6-dimethyl-4-dimethylamino) phenyl-acridine-9-carboxylate (39) (yield=50%).

The dimethylamino ester (39) (154 mg. 0.41 mmole) was dissolved in methylene chloride (2 ml). Methyl fluorosupfate (265 1, 3.28 mmole) was added and the mixture was stirred at room temperature for 15 hours. Amhydrous ether (15 ml) was added and the precipitated solids were filtered and washed with ether. Drying gave (2,6-dimethyl-4-trimethylammonio) phenyl-N-methyl-acridinium-9-carboxylate (40) (yield=50%). MS: FAB, thioglycerol matrix, m/e 400 (M+).

EXAMPLE 10

The compound 3-(2-carboxyethyl)-N-methyl acridinium (2,6-dimethyl-4-nitrophenyl)-9-carboxylate trifluoromethyl sulfonate (N-hydroxy succinimidyl ester), has the formula:

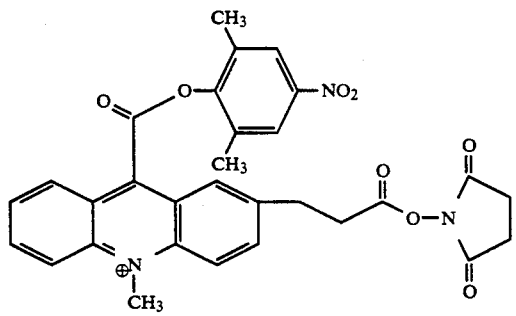

It is made as follows: 4-bromocinnamic acid (Aldrich Chemical Company) (2 g.) was suspended in methanol (10 ml) and platinum oxide (100 mg) was added. The solution was stirred for 4 hours in a hydrogen atmosphere, and the solvent was removed to give a colorless oil (1.8 g, 84%) ms (m/e) 244 (M+), 211,184,121.

nmr (ppm) 7.34, 7.32, 7.07, 7.04. (2 doublets, 4H) 3.31, (3H, singlet) 2.80, 2.57 (multiplets, 4H).

In the reaction, 4-Bromopropionic acid (5 g) was mixed with formanilide (2.25 g), anhydrous K$_2$CO$_3$ and copper bronze (150 mg) in nitrobenzene (17 ml). The mixture was refluxed for 48 hours and the nitrobenzene then removed under vacuum. The resulting brown oil was refluxed in a mixture of acetic acid and conc. HCl (1:1). Extraction into ether, and evaporation of the dried ether solution gave a dark green oil which solidified on standing. The solid was washed with petroleum ether to give a white solid (5 g, 67%) ir 1703 (CO) 3403 (NH) ms (m/e) 241 (M+), 196,182,167.

The previous compound (1.5 g) in carbon disulfide (8 ml) was added slowly over ten minutes to a refluxing solution of oxalyl chloride (1.07 g) in carbon disulfide (6 ml), and refluxing continued for a further one hour. The mixture was evaporated to dryness and carbon disulfide (12 ml) was added. Aluminum chloride (2.88 g) was added in portions, with stirring, and the reaction refluxed for one hour. After removing the solvent, water was added and the product extracted into ether. A red oil was obtained which solidified on standing. (1.3 g, 76%). ir 1734,1677 cm$^{-1}$ (CO) nmr (ppm). The spectra clearly showed the presence, in almost equal amounts, of two isomers. There is no need to separate them, as they both give the same product in the next stage. Peaks at 7.66 to 6.79 (aromatic protons, 8H) multiplets 3.02 to 2.89 (two methylene groups, 4H).

The previously obtained mixture of isatins (1 g) was dissolved in 10% aqueous KOH and refluxed for 18 hours. A yellow precipitate was obtained by acidifying the cooled solution with conc. HCl. The precipitate was collected by filtration and washed with water, methanol and ether (700 mg, 76%) ir (nujol) 1711, 1656 (CO) uv (nm) 388, 370, 358, 340 and 256. nmr (ppm) 12 (broad, 1H) 8.20, 2.18, 8.16, 8.14, 8.13 (2H) 8.06, 8.03 (2H) 7.90, 7.88, 7.84, 7.83 (1H) 3.01, 3.08, 3.06 (2H) 2.07, 2.68, 2.66 (2H)

Analysis: Found (%) C 66.76, H 5.32, N 4.42. C$_{17}$H$_{13}$NO$_4$ requires C 66.86, H 5.57, N 4.11.

The acridine carboxylic acid prepared in the previous step (20 mg) was suspended in re-distilled thionyl chloride (2 ml) and refluxed under an argon atmosphere for 4 hours. The solid (ir 1793 and 1731 cm$^{-1}$ COCl) which resulted after the removal of the thionyl chloride was dissolved in pyridine (1 ml) and N-hydroxy succinimide (6.92 mg) was added. The reaction mixture was stirred under an argon atmosphere for 4 hours, and then cooled in an ice bath. Para-toluene sulfonyl chloride (21.36 mg) was added, and after stirring for 15 minutes, 2,6-dimethyl-4 nitrophenol was added. The reaction was left for 2.5 hours and the pyridine was removed under high vacuum. A few drops of dilute HCl were added and the resulting precipitate was collected by filtration and washed with water and dried (18 mg, 60%). ir (Nujol) 1812, 1781 and 1740 cm$^{-1}$ (CO) uv (nm) 373, 353 and 262. Addition of base caused the hydrolysis of the phenol, giving peaks at 430, 392, 355 and 257.

The acridine ester was dissolved in dichloromethane (2 ml) and methyl triflate (0.5 ml) added. After stirring over night at room temperature, the volatile materials were removed under vacuum, and the residue dissolved in acetonitrile. A yellow solid was precipitated on the addition of ether. ir (Nujol) 1812,1785 and 1745 cm$^{-1}$ uv (MeOH, nm) 369, 354 and 262. Addition of base gave peaks at 430 (p-nitrophenolate) 364, 287 and 257 nm. Thus confirming the structure of 3-(2-Carboxyethyl)-N-methyl acridinium (2,6-dimethyl-4-nitrophenyl)-9-carboxylate trifluoromethyl sulfonate (N-hydroxy succinimidyl ester).

EXAMPLE 11

The compound 3-(2-carboxyethyl(N-methyl acridinium (2,6-dimethyl-4-nitrophenyl)-9-carboxylate trifluoromethyl sulfonate 2,6-dimethyl-4-nitrophenyl ester has the formula:

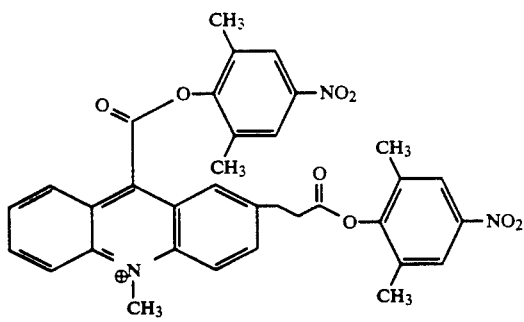

It is made as follows: 3-(2-carboxyethyl) acridine 9-carboxylic acid (20 mg) was dissolved in pyridine (0.5 ml) and the solution cooled in an ice bath. Then p-toluene sulfonyl chloride (51 mg) was added and the solution stirred for 15 minutes. 2,6-Dimethyl-4-nitrophenyl (23 mg) was added and the reaction mixture stirred for 2.5 hours at room temperature. Ice and dilute HCl were added and the resulting yellow precipitate filtered off. Washing with water, ethanol and ether gave a yellow solid (26 mg, 65%). The following analysis was obtained:

ir (nujol) Carbonyl peak at 1746 cm$^{-1}$.
uv (MeOH, HCl) 365, 348, 285 (sh), 262 nm.
ms (m/e) 594 (M+1), 445, 427, 390.

The above diester (25 mg) was suspended in dichloromethane (2 ml) and freshly distilled methyl triflate (0.1 ml) added. The solution became clear dark yellow after 30 minutes. After 18 hours, dry ether was added to the solution, resulting in a yellow precipitate. This was collected by filtration (28 mg, 88%). Its analysis showed:

ir (nujol) Strong carbonyl peak at 1752 cm$^{-1}$.
uv (MeOH) (acid) 368, 353, 263 nm. (base) 430, 364, 287, 257 nm.

Thus confirming the compound 3-(2-Carboxyethyl(N-methyl acridinium (2,6-dimethyl-4-nitrophenyl)-9-carboxylate trifluoromethyl sulfonate 2,6-dimethyl-4-nitrophenyl ester.

The above diester, possessing as it does of a moderately hindered active ester, is suitable for labeling for the analytical purposes described elsewhere in this application. Labeling of the TSH antibody was carried out as previously described, to give labelled antibody with a specific activity substantially identical to that using the previously described esters, resulting in an equivalent immunoassay.

EXAMPLE 12

The compound 2,6-dimethyl-4-nitrophenyl-2-(2-[N-(2,6-dimethyl-4-chlorosulfonyl)phenyl]carboxamidoethyl-N-methylacridinium-9-carboxylate fluorosulfonate has the following formula:

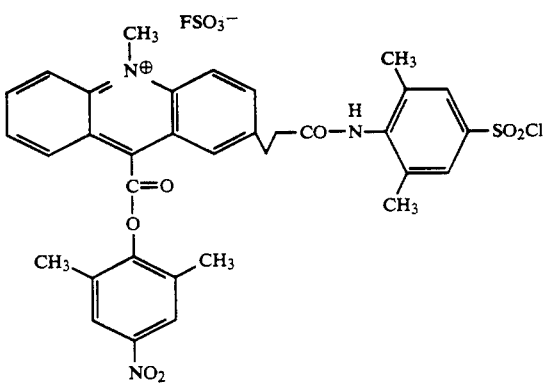

This compound is synthesized from the acridine dicarboxylic acid [2-(2-carboxy)ethyl-acridine-9-carboxylic acid] via a series of transformations. The route for the preparation of 2-(2-carboxy)ethyl-acridine-9-carboxylic acid is shown in the following reaction sequence.

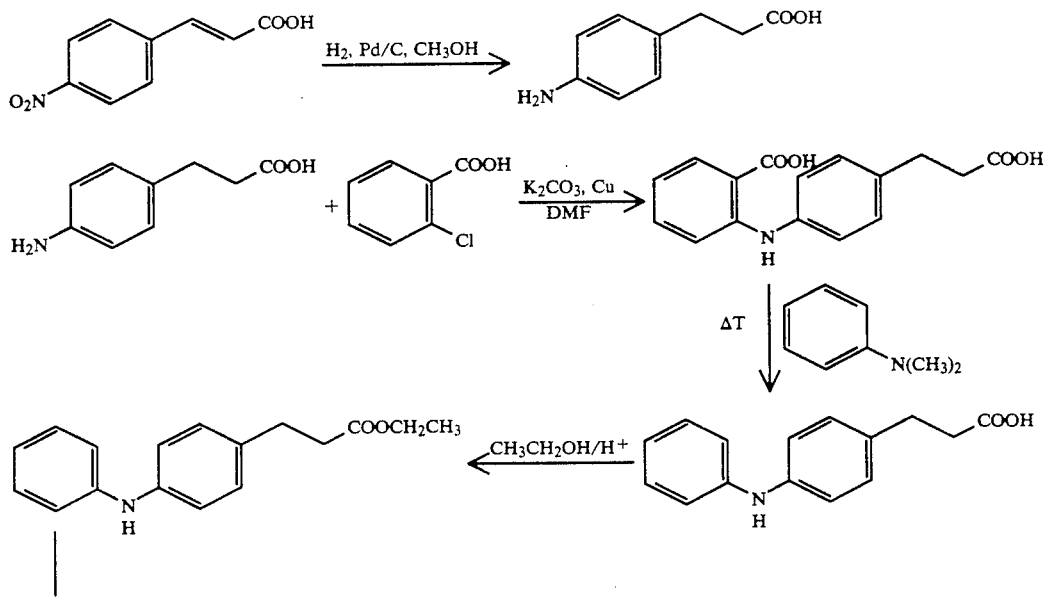

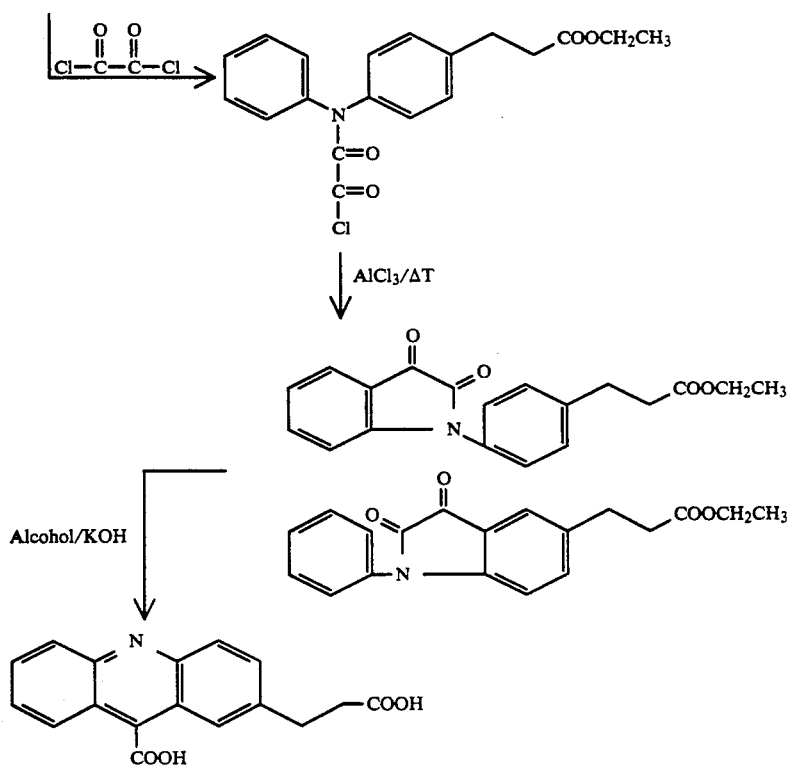
The route for the preparation of 2,6-dimethyl-4-nitrophenyl-2-[2-(2,6-dimethyl-4-chlorosulfonyl-phenylcarbamyl)ethyl]-N-methylacridinium-9-carboxy- late fluorosulfonate, title compound of this example, is detailed in the following reaction sequence.
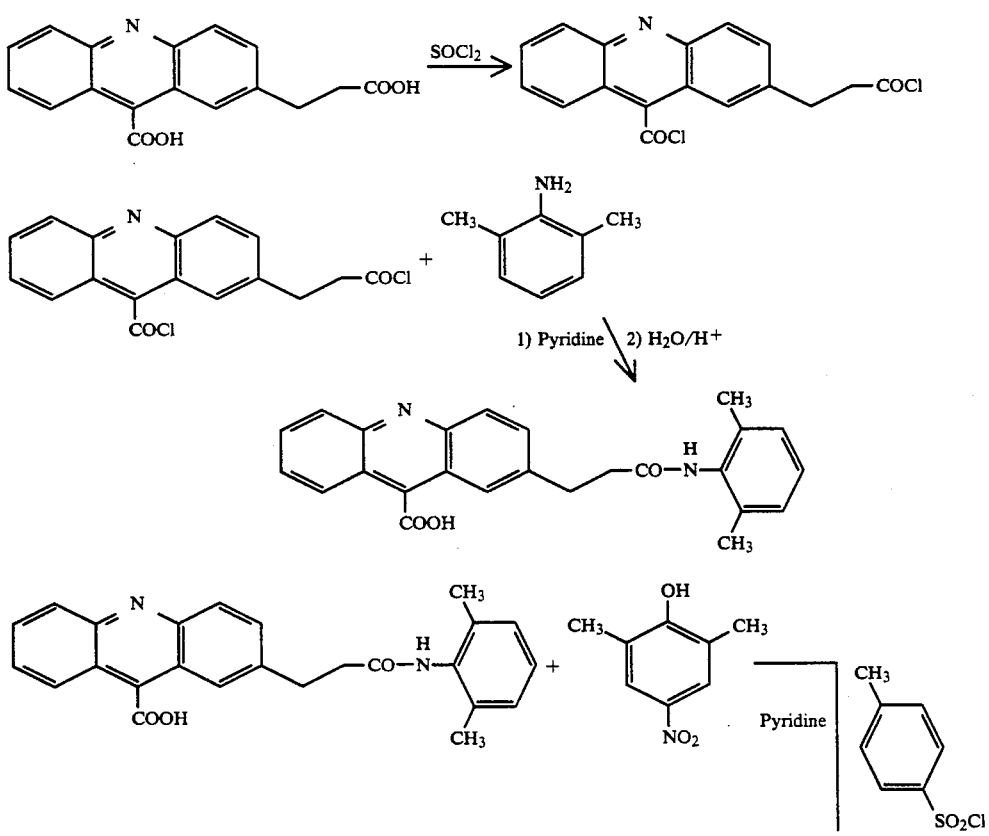

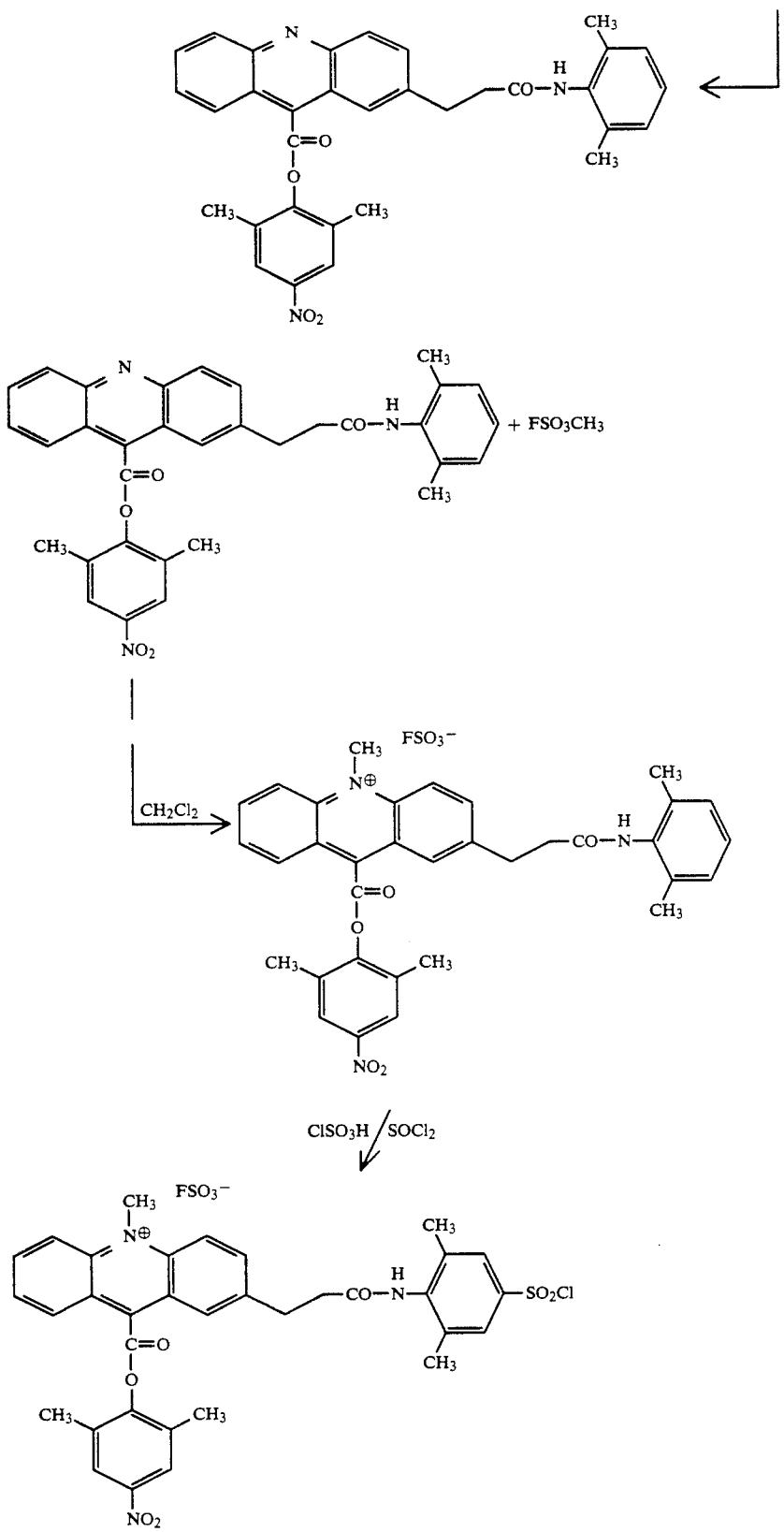
The compositions, p-aminophenylpropionic acid, N-[4-(2-carboxyethyl)]anthranilic acid, N-phenyl-4-aminophenylpropionic acid and ethyl-N-phenyl-4-aminophenylpropionate, were prepared according to the first reaction sequence and all were isolated, purified and characterized by IR, NMR and U.V.

The isatin that was prepared from N-phenyl-ethyl-p-aminophenylpropionate in two steps, as shown in the first reaction sequence of this Example, resulted in two isomers. They were identified by NMR and IR. The data is as follows:

NMR(360 MHz, FT, CD$_3$OD, d PPM): 7.66 ppm to 6.79 ppm (aromatic protons), —CH$_2$ from 4.13 ppm to 4.04 ppm (as multiplet), —CH$_2$ from 3.02 ppm to 2.89 ppm (as two multiplete), another —CH$_2$ (as two triplets) from 2.68 ppm to 2.60 ppm and —CH$_3$ as multiplet from 1.23 ppm to 1.18 ppm.

The compound 2-(2-carboxy)ethylacridine-9-carboxylic acid was prepared from the isatin isomers, as indicated above, in aqueous potassium hydroxide solution. The yield was over 76%. Its characterization is obtainable from the following:

NMR (360 MHzFT, DMSO, d); [8.20 ppm, 8.17 ppm, 8.15 ppm, 8.14 ppm, 8.12] (2H), [8.05 ppm, 8.03 ppm] (d,2H), [7.90 ppm, 7.88 ppm, 7.84 ppm, 7.83 ppm] (1H), [3.10 ppm, 3.08 ppm, 3.06 ppm] (t,2H), [2.70 ppm, 2.68 ppm, 2.66 ppm] (t,2H) and a broad peak at 12 ppm (—H).

M.S.(FAB): m/e 296 (M$^+$+1) IR(nujol) carbonyl peaks at 1711 cm$^{-1}$ and 1656 cm$^{-1}$. U.V. (MeOH) 388 nm, 358 nm, 340 nm, 256 nm, in acid at 362 nm, 346 nm and 272 nm.

| Microanalysis for C$_{17}$H$_{13}$NO$_4$, C$_2$H$_5$OH | | | |
|---|---|---|---|
| | C % | H % | N % |
| Expected | 66.86 | 5.57 | 4.11 |
| Found | 66.76 | 5.32 | 4.42 |

The compound 2-(2-carboxy)ethyl acridine-9-carboxylic acid was chlorinate with thionyl chloride to give the corresponding acid chloride using the procedures described in the preceeding examples.

To a solution of the diacid chloride (200 mg., 0.602 mmoles) in pyridine (4 ml.), 2,6-dimethyaniline (73 mg., 0.603 mmoles) was added. The reaction was stirred at room temperature (23° C.) for 23 hours. After addition of H$_2$O/H$^+$, compound precipitated out, which was filtered, dried and washed with ether. Compound 2-[2-(2,6-dimethyl-phenylcarbamoyl)ethyl]acridine-9-carboxylic acid in over 90% yield, was obtained. Its analysis showed:

M.S.(FAB): m/e 399 (M$^+$+1) IR (nujol): carbonyl peak at 1651 cm$^{-1}$.

This compound was converted to 2,6-dimethyl-4-nitrophenyl-2-[2-(2,6-dimethylphenylcarbamoyl)ethyl]acridine-9-carboxylate

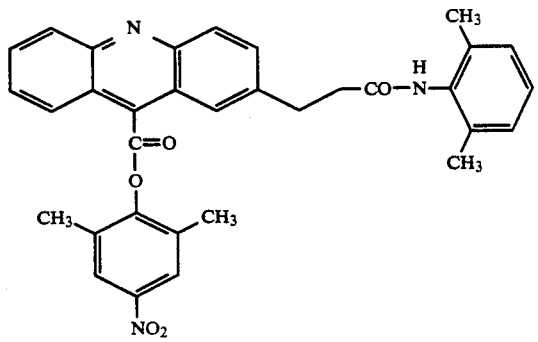

by Brewster's method with over 70% yield. The compound was purified by chromatography. The analysis showed:

UV (MeOH) in H$^+$ p$_i$ 368 nm, 350 nm, 264 nm and in base, at 430 nm, 392 nm, 363 nm and 256 nm.

IR (nujol): carbonyl peaks at 1748 cm.$^{-1}$ and 1659 cm.$^{-1}$ NMR (500 MHz, CDCl$_3$, 5): aromatic protons from 8.45 ppm to 6.6123 ppm, two triplets at [3.39 ppm, 3.37 ppm, 3.36 ppm], (2H), [2.91 ppm, 2.89 ppm, 2.88 ppm], (2H), a singlet at 2.52 ppm (6H) and another singlet at 2.03° ppm (6H).

N-methylation of the compound

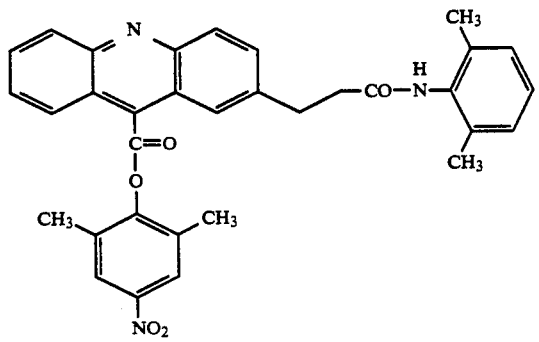

with methyl fluorosulfonate, resulted, 2,6-dimethyl-4-nitrophenyl-2[2-(2,6-dimethylphenylcarbamoyl)ethyl]-N-methylacridinium-9-carboxylate with over 80% yield. Its structure was supported by the following data:

M.S. (FAB), 562 m/e (m$^+$+1) U.V.(MeOH) in H$^+$, shows peaks at 374 nm, 355 (sh), 266 nm, in OH, at 430 nm, 330 nm (sh), 185 nm, 252 nm.

The compound

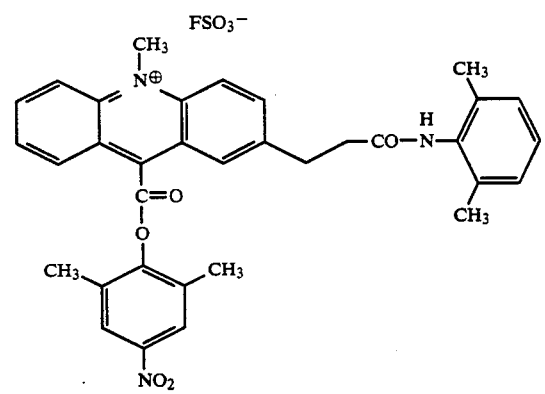

was converted to 2,6-dimethyl-4-nitrophenyl-2-[2-(2,6-dimethyl-4-chlorosulfonyl-phenylcarbamoyl)ethyl]-N-methylacridinium-9-carboxylate fluorosulfonate in chlorosulfonic acid and thionylchloride with over 70% yield. Analysis:

M.S. (FAB): 660 m/e (m$^+$+1) U.V.(MeOH) in H$^+$, shows peaks at 373 nm, 356 nm, 266 nm, in OH, at 425 nm, 288 nm, 255 nm.

EXAMPLE 13

An illustrative conjugate of the present invention comprises progesterone bound to (2,6-dimethoxy-3-chlorosulfonyl)phenyl-N-methyl-acridinium-9-carboxylate fluorosulfonate characterized by the following formula:

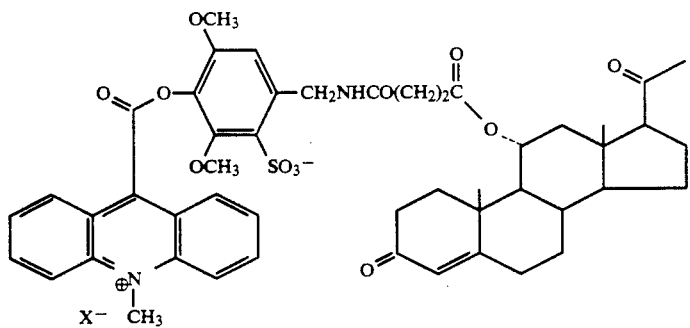
The progesterone conjugate is synthesized according to the following scheme:
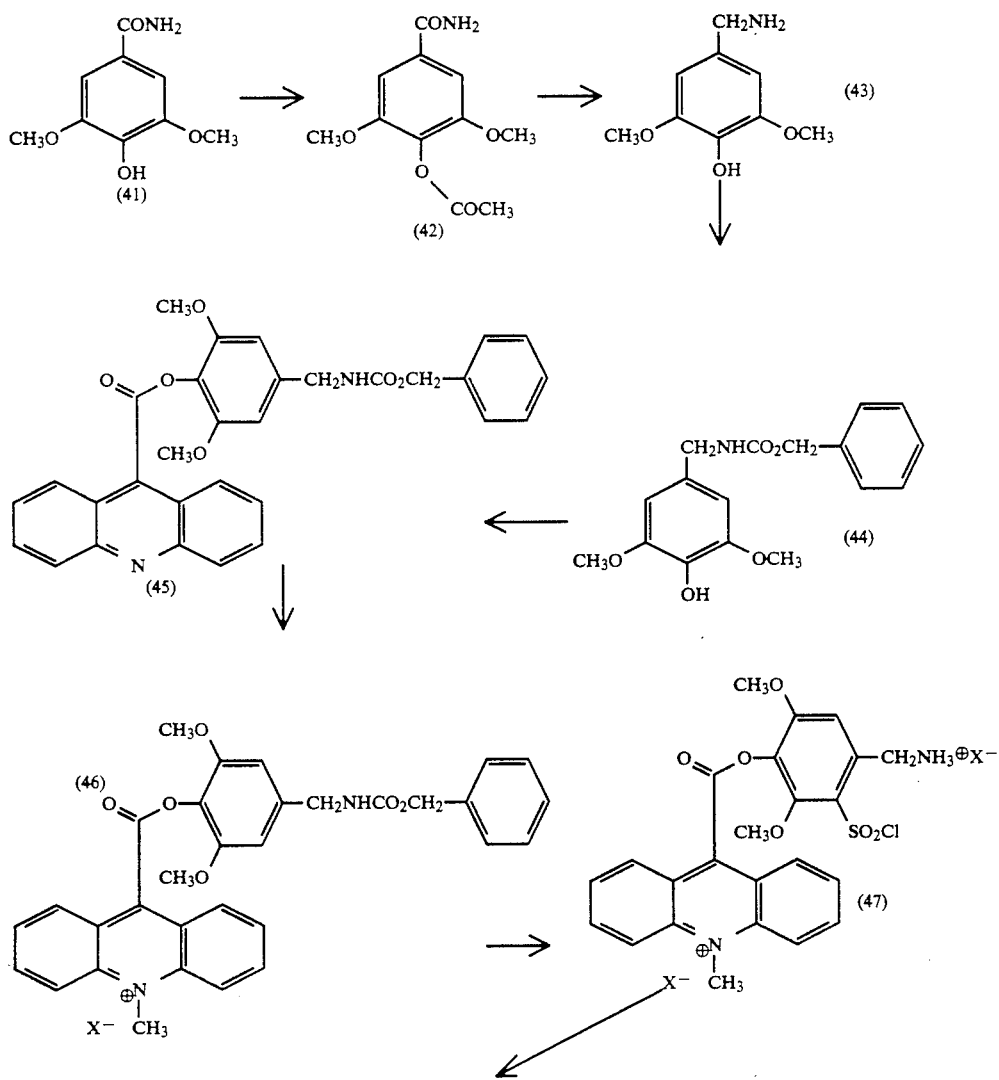

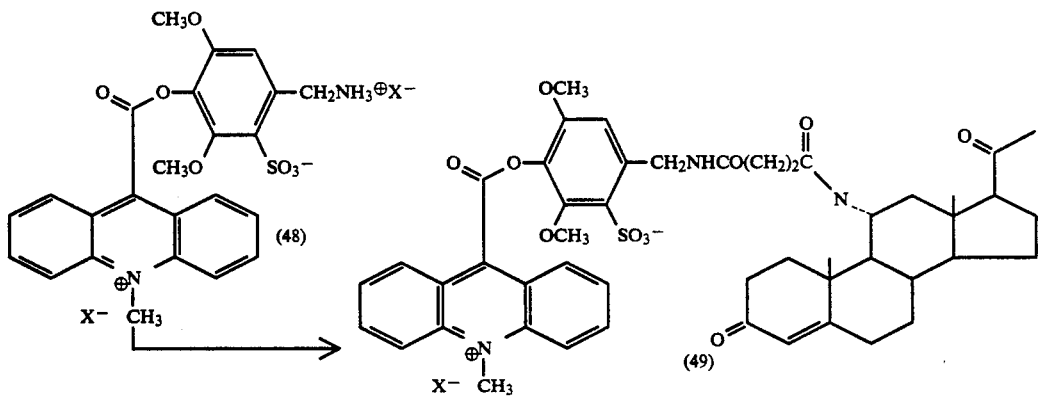

In the reaction scheme, 3,5-dimethoxy-4-hydroxy benzamide (41) (3.0 g, 15.2 mmole) was dissolved in anhydrous pyridine (15 ml) and the solution was cooled in a dry ice/CCl4 bath. Acetyl chloride (1.4 ml, 1.54 g, 19.7 mmole) was added and the mixture was kept stirred at room temperature for 2 hours. Methanol (1 ml) and water (5 ml) were added and the solvents were removed under reduced pressure. The residue was treated with water (50 ml) acidified with dilute hydrochloric acid and was extracted with ethyl acetate. Washing with water, drying and evaporating of the ethyl acetate gave 2,6-dimethoxy-4-carboxamido-phenyl acetate (42) (2.2 g) which was recrystallized from ethyl acetate (yield=60%).

The phenyl acetate (42) (1.27 g, 5.33 mmole) was dissolved in anhydrous tetrahydrofuran (125 ml). Diborane solution in THF (1.0M, 10.9 ml, 10.9 mmoles) was added and the mixture was refluxed for 4 hours. After cooling to room temperature water (2 ml) and hydrochloric acid (1.0N, 5 ml) were added. After stirring for 30 minutes the solvents were removed in vacuum. The residue was extracted with chloroform. The chloroform was then dried and removed in vacuo. 2,6-dimethoxy-4-aminomethylphenol (43) was used in the next step without further purification.

To a solution of the crude amine (43) in anhydrous pyridine (10 ml) benzylchloroformate (1.050 ml, 1.25 g, 7.3 mmole) was added and the mixture was stirred for 3 hours at room temperature. Water (5 ml) was added and the solvents were removed in vacuo. To the residue water (30 ml) was added and the mixture was acidified with dilute HCl. Extraction with ethyl acetate, washing with water, drying and evaporation of the solvent gave 2,6-dimethoxy-4-(benzyloxycarbonylamino)methyl phenol (44) as an oil (yield=70% overall).

Acridine-9-carboxylic acid (754 mg, 3.38 mmole) was dissolved in anhydrous pyridine (14 ml). Para-toluene sulfonyl chloride (1.28 g, 6.76 mmole) was added and the mixture was stirred at room temperature for 30 minutes. 2,6-dimethoxy-4-(benzyloxy carbonylamino)-methyl phenol (44) (1.18 g, 3.76 mmole) was added and the mixture was stirred at room temperature for 15 hours. Water (10 ml) was added and solvents were removed in vacuo. The residue was dissolved in chloroform and the chloroform layer was washed successively with water, 0.1N HCl and sodium bicarbonate solution. Drying and evaporating of chloroform gave the crude ester which was chromatographed on a silica gel column using CHCl3/Ethyl acetate, 1:1, as the solvent. Evaporation of the solvents from the pooled fractions gave [2,6-dimethoxy-4-(benzyloxycarbonylamino)methyl]phenyl-acridine-9-carboxylate (45) (yield=22%).

The acridine (45) (296 mg, 0.57 mmole) was dissolved in anhydrous methylene chloride (5 ml). Methyl fluorosulfate (277 µl, 3.4 mmole) was added and the mixture was stirred at room temperature for 5 hours. Anhydrous ether (25 ml) was added and the precipitated [2,6-dimethoxy-4-(benzyloxycarbonyl amino)methyl]phenyl-acridinium-9-carboxylate fluorosulfonate (46) was filtered and washed with ether and dried (yield=99%).

The acridinium (46) (107 mg, 0.169 mmole) was suspended in anhydrous methylene chloride (2 ml). Chlorosulfonic acid (53 µl, 92 mg, 0.797 mmole) was added after the flask was cooled in a dry ice/CCl4 bath. It was stirred for 30 minutes and the bath was removed. After further stirring at room temperature for 1.5 hours anhydrous ether (20 ml) was added. The precipitated product was filtered and dried in vacuo. The (2,6-dimethoxy-4-aminomethyl-3-chlorosulfonyl)phenyl-acridinium-9-carboxylate fluorosulfonate (47) was directly used in the next reaction.

The sulfonyl chloride (47) (129 mg) was stirred at room temperature in a mixture of methanol (12.5 ml) and water (12.5 ml) for 3 hours. Acetonitrile (35 ml) was added and the solvents were evaporated. The residue was dried in vacuum over phosphorous pentoxide. The (2,6-dimethoxy-4-aminomethyl-3-oxosulfonyl)phenyl-acridinium-9-carboxylate fluorosulfonate (48) was used directly for the next reaction. The same results may be achieved by crystallization from acetonitrile by the addition of ethyl acetate. Other useful solvent combinations include alcohol and ether, such as methanol, ethanol or propanol and diethyl ether (ether is the precipitating solvent). In addition, compound (41) may be further treated with thionyl chloride, as indicated above, to increase the sulfonyl content of the compound, if desired.

Progesterone hemisuccinate (90 mg, 0.209 mmole) and N-methylmorpholine (22 µl, 209 mmole) were dissolved in anhydrous DMF (2 ml). The solution was chilled in dry ice/CCl4 bath and isobutylchloroformate (30 µl, 0.229 mmole) was added. After 2 minutes a solution of the acridinium (42) (101 mg, 0.143 mmole) in dimethylsulfoxide (2 ml) containing N-methylmorpholine (3.14 µl, 0.28 mmole) was added. Stirring was continued at −20° C. for 10 minutes and the cooling bath was removed. After stirring at room temperature for 7 hours, 3 drops of water were added. The solvents were removed in vacuo and ethyl acetate was added to the residue. The oily precipitate was washed repeatedly with ethyl acetate. Upon trituration with acetonitrile (2 ml) the oil separated as solids. The product was purified on HPLC using C18 Dynamax semi-prep column (10 mm×250 mm) (commercially available from Rainin Instrument Co., Inc., Woburn, Mass.) using CH3CN/H2O (0.1% trifluoroacetic acid), 55/45 as mobile phase at a flow rate of 2.75 ml/min. The peak appearing at retention time of 6.00 minutes was collected. Evaporation of solvents gave the conjugate (43) (yield=30%). MS: FAB, thioglycerol matrix, 895 (M+, without any counterions).

EXAMPLE 14

The following procedure for attaching to protein is generally applicable to chemiluminescent labels of the present invention.

Mouse IgG (Sigma, 1 mg) was dissolved in 0.9 ml phosphate buffer (100 mM, pH 8.0, 150 mM). If desired, higher pH may be employed, such as a pH as high as 9.5. The solution was then divided into three equal portions of 0.33 mg/0.3 ml (0.0022 μmoles). About 0.3 mg of a moiety of the present invention was dissolved in about 0.4 ml DMF so as to obtain 0.022 μmoles of moiety in 15 μl DMF.

0.022 μmoles of the compound of the present invention was mixed with 0.0022 μmoles of IgG in a plastic microcentrifuge tube. After 15 minutes, an additional 0.022 μmoles of compound was added to the microcentrifuge tube (compound to protein molar ratio was 20:1). After an additional 15 minutes, excess amounts of the compound of the present invention were quenched with lysine HCl solution (10 μl in 100 mM p; buffer, pH 8.0) for 15 minutes.

Alternatively, aliquots of 0.0055 μmoles of the compound of the present invention was used instead of 0.022 μmoles (compound to protein molar ratio was 5:1).

Biorad glass columns (1 cm×50 cm) (commercially available from Biorad, Chemical Division, Richmond, Calif.) were packed with previously swelled and deaerated Sephadex G-50-80 in phosphate buffer (100 mM, pH 6.3, 150 mM NaCl, 0.001% TMS) to a bed volume of 45 ml. The reaction solution was run through the columns at a flow rate of 0.3-0.4 ml/min. 0.5 ml fractions were collected. Labelled protein fractions were detected by diluting 20 μl from each fraction to 1 ml and determining the chemiluminescence produced with 30 μl of the diluted solution. Labelled fractions were then pooled.

The pooled conjugate fractions were dialyzed to improve the purity of immunoreactive conjugate. The pooled fractions were dialyzed against 500 ml pH 6.3 phosphate buffer (100 mM, pH 6.3, 150 mM NaCl, 0.001% TMS) over a period of 24 hours with three buffer changes.

General labeling procedure for sulfonyl chloride based acridinium esters.

Anti-TSH antibody (1 mg) is transferred to a Centricon 30 (ultrafiltration unit, Amicon, Beverly, Mass.) and 1 ml bicarbonate buffer (15 mM, pH 9.6) is added. The buffer is centrifuged and the volume of solution brought up to 400 μl using the same buffer. A solution of the compound of Example 4 of the formula

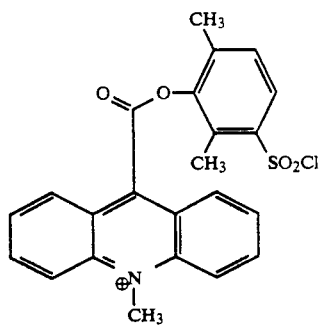

in DMF (N,N-dimethylformamide, 2 mg/mL, 21.6 μl) is added to the anti-TSH antibody and the Centricon is gently mixed for 15 minutes by hand. Another 21.6 μl from a freshly made DMF solution of the same compound, is added at the end of 15 minutes. A total of 24 moles pf the compound to antibody, is used in the reaction. Fifteen minutes from the second addition, the protein solution is purified from the unreacted compound using a Sephadex desalting column (Pharmacia HR-10/10), an HPLC system, and a eluent solvent comprising 1 part ethanol and 4 parts phosphate buffer (100 mM sodium phosphate, 300 mM sodium chloride, pH 6.0). The protein fraction is collected and the eluent solvent is exchanged with phosphate buffer (pH 6.3) in a Centricon 30. The concentrate acridinium labelled anti-TSH antibody is diluted into 25 ml of diluent buffer (sodium phosphate buffer 100 mM, sodium chloride 150 mM, Thimerosal 0.001%, 0.4% BSA, 0.1 mg/ml each (0.001%) of mouse and goat £-globulins, pH 6) after filtration through a 0.45 micron syringe filter. The diluted 25 milliliters is stored at −20° C. as a stock solution to make TSH labelled antibody reagent after appropriate dilutions.

ASSAY PROTOCOLS

EXAMPLE 15

1. Components

A) Labelled Antibody (conjugate): Affinity purified rabbit antiprolactin conjugated to (2,6-dimethoxy-3-chlorosulfonyl)phenyl-N-methyl-acridinium-9-carboxylate fluorosulfonate. Storage buffer: 10 mM phosphate buffer, 100 mM NaCl pH 6.0, 0.001% Thimerosal, 0.4% BSA.

B) Capture antibody: Rabbit anti-prolactin (6 μg/ml) as a solid phase on Nunc tubes (commercially available from Midland Scientific, Roseville, Minn.).

C) Solid-phase coated tubes: Dried Nunc tubes were prepared as follows:
1) 0.3 ml of the capture antibody per tube at 6 μg/ml in PBS buffer (phosphate buffer saline, pH 7.2-7.4, 10 mM phosphate, 100 mM NaCl, 10 mM NaN3) was pipetted into Nunc tubes.
2) Tubes were incubated for 18-24 hours.
3) Tubes were washed 2 times with the PBS buffer.
4) Tubes were blocked with 2.0% BSA in PBS buffer. Incubate for <4 hours at room temperature.
5) Tubes were washed 3 times with PBS buffer.
6) Tubes were dried at room temperature.
7) Tubes were stored in plastic freezer bags at 4° C.

D) Standards: Prepared in horse serum 0, 5, 30, 100 and 200 ng/ml/ml

2. Assay Protocol 1) 25 μl of sample or standard was pipetted into the antibody-coated tubes. 2) 100 μl of labelled antibody was added. 3) Tubes were vortexed gently. 4) Tubes were incubated for 1 hour at room temperature on a rotator. 5) Tubes were washed 3 times with deionized water. 6) Chemiluminescence was counted for 2 seconds [pump 1: 0.1N $HNO_3$+0.25% $H_2O_2$; pump 2: 0.25N NaOH+0.125% CTAC] in a LumaTag ™ Analyzer (commercially available from London Diagnostics, Eden Prairie, Minn.).

EXAMPLE 16

1. Components

A) Progesterone Conjugate of a b-D-thioglucose adduct of (2,6-dimethoxy-3-chlorosulfonyl)phenyl-N-methyl-acridinium-9-carboxylate fluorosulfonate: 20 pg/ml progesterone conjugate in phosphate buffer (pH 6.0, 100 mM phosphate, 150 mM NaCl, 0.1% human serum albumin, 0.001% Thimerosal).

B) Primary antibody: Rabbit anti-progesterone (Cambridge Medical Diagnostics) in phosphate buffer (pH 6.0, 200 mM phosphate, 150 mM NaCl, 0.1% human serum albumin, 0.01% CHAPS, 5 μg Danazol).

C) Solid-phase coated tubes: Dried Nunc tubes coated with 2.5 μg of Goat anti-Rabbit fc and blocked with 0.5% BSA. Tubes were prepared as follows:
1) Tubes were incubated for 1 hour with 2.5 μg/ml Goat anti-Rabbit fc (500 μl) at room temperature.
2) Tubes were washed 3 times with distilled water.
3) Tubes were immediately incubated for 3 hours with 0.5% BSA (500 μl) at room temperature.
4) Tubes were washed 3 times with distilled water.
5) Tubes were dried overnight at 40% relative humidity at room temperature.
6) Tubes were stored in plastic freezer bags at 4° C.

D) Serum matrix: Antech steer serum.

E) Standards: 0, 0.13, 0.38, 1.31, 7.31 16.6 and 37.0 ng/ml.

2. Assay Protocol 1) 50 μl of sample or standard was pipetted into the antibody-coated tubes.
2) 100 μl of conjugate buffer was added.
3) 100 μl of primary antibody buffer was added.
4) Tubes were vortexed gently.
5) Tubes were incubated for 2 hours at 37° C.
6) Tubes were decanted and washed with 150 mM NaCl in 0.1% Tween (1 ml) and then 3 times with distilled water.
7) Tubes were inverted and allowed to drain.
8) Chemiluminescence was counted for 2 seconds[pump 1: 0.1N $HNO_3$+0.25% $H_2O_2$; pump 2: 0.25N NaOH+0.125% CTAC] in a LumaTag ™ Analyzer (commercially available from London Diagnostics, Eden Prairie, Minn.).

EXAMPLE 17

1. Components

A) Labelled Ab: Affinity purified goat anti-TSH conjugated to (2,6-dimethoxy-3-chlorosulfonyl)phenyl-N-methyl-acridinium-9-carboxylate fluorosulfonate.

B) Storage buffer: 100 mM phosphate, 0.145M NaCl, 0.001% Thimerosal, 0.4% BSA, 0.1 mg/ml mouse-globulins, and 0.1 mg/ml goat-globulins, pH 6.0.

C) Capture antibody: Monoclonal-anti-TSH (2 μg/ml) as a solid phase on Nunc tubes. Procedure for preparation of solid-phase Nunc tubes:
1) 0.4 ml of the capture antibody at 2 μg/ml in PBS buffer (phosphate buffer saline, pH 7.2-7.4, 10 mM phosphate, 100 mM NaCl, 10 mM $NaN_3$) was added to each tube.
2) Tubes were incubated for 18-24 hours.
3) Tubes were washed 3 times with the PBS buffer.
4) Tubes were blocked with 2.0% BSA in PBS buffer and incubated for <4 hours at room temperature.
5) Tubes were washed 3 times with PBS buffer.
6) Tubes were dried at room temperature.
7) Tubes were stored in plastic freezer bags at 4° C.

D) Standards: Prepared in horse serum.0, 0.5, 2.5, 10, 25 and 100 μIU/ml

2. Assay Protocol 1) 200 μl of sample was pipetted into the coated tubes.
2) 100 μl of labelled antibody was added.
3) Tubes were vortexed gently.
4) Tubes were incubated for 2 hours at room temperature on a shaker.
5) Tubes were washed using a Biotomic washer (commercially available from Ocean Scientific, Inc., Garden Grove, Calif.).
6) Chemiluminescence was counted for 2 seconds [pump 1: 0.1N $HNO_3$+0.25% $H_2O_2$; pump 2: 0.25N NaOH+0.125% CTAC] in a LumaTag ™ Analyzer (commercially available from London Diagnostics, Eden Prairie, Minn.).

EXAMPLE 18

1. Components

A) Labelled Ab: Affinity purified rabbit anti-prolactin conjugated to (2,6-dimethyl-4-nitro)phenyl-N-methyl-acridinium-9-carboxylate fluorosulfonate. Storage buffer: 10 mM phosphate buffer, 100 mM NaCl pH 6.0, 0.001% Thimerosal, 0.4% BSA.

B) Capture antibody: Rabbit anti-prolactin (6 μg/ml) as a solid phase on Nunc tubes.

C) Solid-phase coated tubes: Dried Nunc tubes were prepared as follows:
1) 0.3 ml of the capture antibody per tube at 6 μg/ml in PBS buffer (phosphate buffer saline, pH 7.2-7.4, 10 mM phosphate, 100 mM NaCl, 10 mM $NaN_3$) was pipetted into Nunc tubes.
2) Tubes were incubated for 18-24 hours.
3) Tubes were washed 2 times with the PBS buffer.
4) Tubes were blocked with 2.0% BSA in PBS buffer. Incubate for <4 hours at room temperature.
5) Tubes were washed 3 times with PBS buffer.
6) Tubes were dried at room temperature.
7) Tubes were stored in plastic freezer bags at 4° C.

D) Standards: Prepared in horse serum 0, 5, 30, 100 and 200 ng/ml/ml

2. Assay Protocol 1) 25 μl of sample or standard was pipetted into the antibody-coated tubes.
2) 100 μl of labelled antibody was added.
3) Tubes were vortexed gently.
4) Tubes were incubated for 1 hour at room temperature on a rotator.
5) Tubes were washed 3 times with deionized water.
6) Chemiluminescence was counted for 2 seconds [pump 1: 0.1N $HNO_3$+0.25% $H_2O_2$; pump 2: 0.25N NaOH+0.125% CTAC] in a LumaTag ™ Analyzer (commercially available from London Diagnostics, Eden Prairie, Minn.).

Labelling Of TSH Antibody With 2,6-dimethyl-4-nitrophenyl-2-[2-(2,6-dimethyl-4-chlorosulfonyl-phenylcarbamoyl)ethyl]-N-methylacridinium-9-carboxylate fluorosulfonate Anti-TSH antibody was labelled with the compound

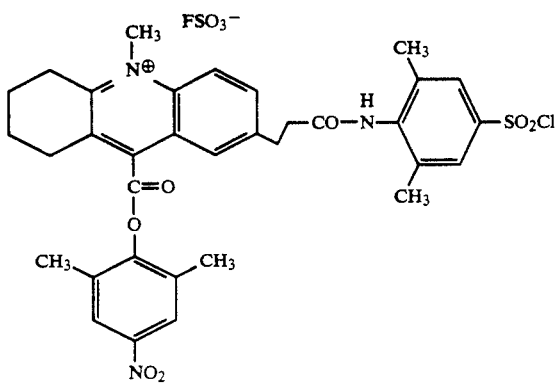

according to the method of Example 14 that is described previously for

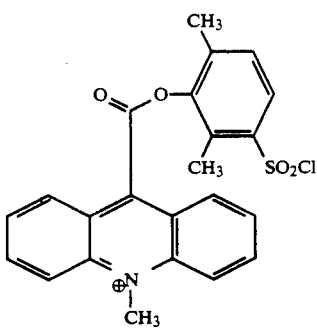

In the reaction, 250 μg (24.7 μl) of Anti-TSH antibody and 2×12 excess moles of the compound were added in 15 minute intervals. At the end the addition, and after purification, the labeled antibody was diluted to 6.25 ml. with the diluent buffer solution and used as stock solution. 100 ml of labeled antibody (stock solution) was diluted with 0.6 ml. of antibody diluent.

TSH assays were carried out using the reagents from a LumaTag ™ TSH kit and substituting the above labeled TSH antibody reagent, comparable results were obtained to that obtained using instead a labeled TSH where the label is the compound of Example 4.

EXAMPLE 19

A solution of 2,6-dimethyl-3-chlorosulfonyl phenyl acridinium-9-carboxylate fluorosulfonate (0.355 mg.) in a mixture of 188 μl acetonitrile and 100 μl DMF was placed in a 2 ml clear screw-capped vial. A solution of glycine benzyl ester p-toluene sulfonate salt (2.63 mg) in 150 μl acetonitrile containing 0.71 μl triethylamine was prepared. The two solutions were mixed and left standing for 1 hour and 15 minutes at room temperature (about 23° C.). The reaction product was isolated and purified on an HPLC system using a $C_{18}$ reverse phase column and acetonitrile:water (0.1% trifluoroacetic acid) in a ratio of 60/40 as the mobile phase. The isolated product had the formula

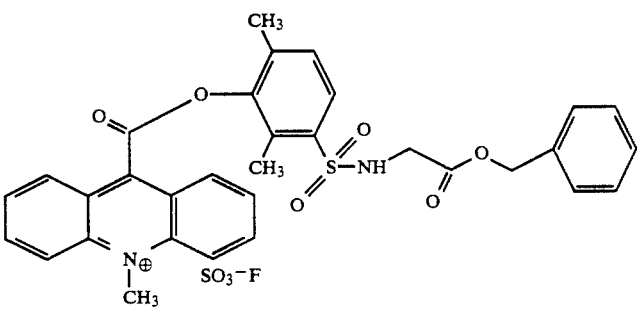

From the foregoing, it will be obvious to those skilled in the art that various modifications in the above-described compositions and methods can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A novel chemiluminescent compound comprising a aryl ester, thioester or amide of a carboxylic acid substituted heterocyclic ring that is susceptible to chemical attack to dissociate the heterocyclic ring to a transient compound, wherein the heterocyclic ring is ring carbon-bonded to the carbonyl of the ester, thioester or amide moiety and possesses a heteroatom in an oxidation state that allows chemiluminescence by dissociating a compound at the carbon bonded to the carbonyl that decays to produce chemiluminescence, the aryl is a ring or ring system that is ring carbon-bonded to the oxygen, sulfur or nitrogen of the ester, thioester or amide, as the case may be, and contains diortho electron donating substitution in conjunction with meta and/or para substituents that possess a $\sigma_p$ value greater than 0 and less than 1.

2. A novel chemiluminescent labeling compositions comprising an ester, thioester or amide covalently and jointly bonded to (1) a carbon of a heterocyclic ring or ring system that is susceptible to attack by peroxide or molecular oxygen and (2) an aryl ring or ring system wherein the heterocyclic ring or ring system is distinquished by a heteroatom thereof an oxidation state that causes the attacked carbon atom to chemiluminesce; the aryl ring or ring system contains at least three substituents, two of which are ortho substituents that are electron donating and at least one of which is a meta or para substituent that possesses a $\sigma_p$ value greater than 0 and less than 1.

3. A hydrolytically stable heterocyclic composition capable of chemiluminescent properties when labeled to a specific binding material by chemically-induced dissociation, and contains
   (a) an aryl ring,
   (b) a sterically-hindered ester, thioester or amide linkage moiety with enhanced hydrolytic stability, and
   (c) a heterocyclic organic ring moiety, in which
      (1) the carbonyl carbon of (b) is covalently bonded to a carbon atom (x) of (c) and the remaining free valence of (b) is carbon bonded to an aromatic ring carbon atom (y) of (a),
      (2) (a) comprises at least three substituent groups hindering hydrolysis of (b), two of which are electron donating and located on the ring carbon atoms adjacent to (y), the remainder are meta and/or para to (y) and electron withdrawing with a $\sigma_p$ value greater than 0 and less than 1, and
      (3) (c) comprises
         (i) at least one ring carbon atom adjacent to said ring carbon atom (x), and
         (ii) a ring member heteroatom in an oxidation state that provides such chemiluminescence properties.

4. A hydrolytically stable conjugate possessing chemiluminescent properties by chemical dissociation, comprising a chemiluminescent label bonded to a specific binding material that contains
   (a) an aryl ring,
   (b) a sterically-hindered ester, thioester or amide linkage moiety with enhanced hydrolytic stability, and
   (c) a heterocyclic organic ring moiety, in which
      (1) the carbonyl carbon of (b) is covalently bonded to a carbon atom (x) of (c) and the remaining free valence of (b) is carbon bonded to an aromatic ring carbon atom (y) of (a),
      (2) (a) contains at least three substituent groups hindering hydrolysis of (b), two of which are electron donating and located on the ring carbon atoms adjacent to (y), the remainder are meta and/or para to (y) and electron withdrawing with a $\sigma_p$ value greater than 0 and less than 1 , and
      (3) (c) contains
         (i) at least one ring carbon atom adjacent to said ring carbon atom (x), and
         (ii) a ring member heteroatom that is in an oxidation state whereby reaction of molecular oxygen or a peroxide with said composition forms an intermediate which decays to produce chemiluminescence.

5. The chemiluminescent labeling composition of claim 1 conjugated with a specific binding material.

6. A chemiluminescent assay comprising the conjugate of claim 4.

7. A chemiluminescent assay kit comprising the conjugate of claim 5.

8. A hydrolytically stable heterocyclic composition capable of chemiluminescent properties when labeled to a specific binding material, by reaction with peroxide or molecular oxygen, comprising
   (a) an aryl ring,
   (b) a sterically-hindered ester, thioester or amide linkage moiety with enhanced hydrolytic stability, and
   (c) a heterocyclic organic ring moiety, in which
      (1) the carbonyl carbon of (b) is covalently bonded to a carbon atom (x) of (c) and the remaining free valence of (b) is carbon bonded to an aromatic ring carbon atom (y) of (a),
      (2) (a) contains at least three substituent groups hindering hydrolysis of (b), two of which are electron donating and located on the ring carbon atoms adjacent to (y), the remainder are meta and/or para to (y) and electron withdrawing with a $\sigma_p$ value greater than 0 and less than 1, and
      (3) (c) contains
         (i) at least one ring carbon atom adjacent to said ring carbon atom (x), and
         (ii) a ring member heteroatom in an oxidation state that provides such chemiluminescence properties.

9. A hydrolytically stable conjugate possessing chemiluminescent properties by reaction of molecular oxygen or a peroxide therewith, comprising a chemiluminescent label bonded to a specific binding material that contains
   (a) an aryl ring,
   (b) a sterically-hindered ester, thioester or amide linkage moiety with enhanced hydrolytic stability, and
   (c) a heterocyclic organic ring moiety, in which
      (1) the carbonyl carbon of (b) is covalently bonded to a carbon atom (x) of (c) and the remaining free valence of (b) is carbon bonded to an aromatic ring carbon atom (y) of (a),
      (2) (a) contains at least three substituent groups hindering hydrolysis of (b), two of which are electron donating and located on the ring carbon atoms adjacent to (y), the remainder are meta and/or para to (y) and electron withdrawing with a $\sigma_p$ value greater than 0 and less than 1, and
      (3) (c) contains
         (i) at least one ring carbon atom adjacent to said ring carbon atom (x), and
         (ii) a ring member heteroatom that is in an oxidation state whereby reaction of molecular oxygen or a peroxide with said composition forms an intermediate which decays to produce chemiluminescence.

10. An assay for the presence of an analyte in a sample comprising contacting an analyte with the chemiluminescent-labeled specific binding material of claim 9, inducing chemiluminescence by decay of an intermediate formable in the presence of peroxide or molecular oxygen, and measuring chemiluminescence therefrom to assay the analyte.

11. A specific binding assay kit comprising a vial containing a conjugate possessing chemiluminescent properties by reaction of molecular oxygen or a peroxide therewith and containing the chemiluminescent label bonded to a specific binding material of claim 9.

12. The novel chemiluminescent compound of claim 1 wherein the heterocyclic ring is from the group consisting of acridinium, benz[a]acridinium, benz[b]a- cridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

13. The novel chemiluminescent compound claim 2 wherein the heterocyclic ring is from the group consisting of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

14. The hydrolytically stable heterocyclic composition of claim 3 wherein the heterocyclic ring is from the group consisting of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

15. The hydrolytically stable heterocyclic composition of claim 8 wherein the heterocyclic ring is from the group consisting of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

16. The novel chemiluminescent compound of claim 1 wherein it has the formula:

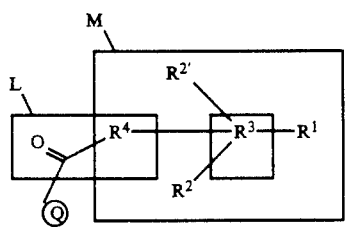

in which L contains the ester, thiolester or amide linkage which is carbon-bonded between two substituted rings or ring systems Q and $R^3$; $R^4$ is —O—, —S— or —NT—; T is a stable nitrogen bonded group; M is a leaving group comprising a portion of L and moiety $R^3$ with its associated $R^1$, $R^2$ and $R^{2'}$ bonded thereto; $R^3$ is an aryl group covalently bonded to $R^4$; $R^1$ is an electron withdrawing group with a $\sigma_p$ value greater than 0 and less than 1 that is bonded meta and/or para to the carbon of $R^3$ bonded to $R^4$; $R^2$ and $R^{2'}$ are bulky electron donating groups bonded ortho to the bond of $R^4$ to $R^3$; M is a leaving group which possesses a $pK_a$ of about $\leq 11$; Q is a heterocyclic ring or ring system to which the ester, thiolester or amide linkage L is attached at a carbon atom within the heterocyclic ring or ring system, which carbon atom (1) is either $sp^2$ or $sp^3$ hybridized, and (2) is susceptible to attack by peroxide or molecular oxygen to form the intermediate that decays to produce chemiluminescence, the oxidation state of the heteroatom within the heterocyclic ring or ring system determining whether the carbon atom is susceptible to such attack and if the carbon to which the linkage is attached is $sp^2$ hybridized, the heteroatom is in a positive oxidation state, and if the carbon to which the linkage is attached is $sp^3$ hybridized, the heteroatom is in a neutral oxidation state, and where the heteroatom is nitrogen, the nitrogen is substituted with an alkyl group or a reactive functionalized alkyl group, an aryl group or a reactive functionalized aryl group, —O— where the nitrogen is in a positive oxidation state or —OH where the nitrogen is in a neutral oxidation state, such that the carbon atom is susceptible to attack by peroxide or molecular oxygen to produce a chemiluniscent intermediate.

17. The novel chemiluminescent compound of claim 16 wherein the heterocyclic rings or ring systems that contain the heteroatom in a positive oxidation state are from the group consisting of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium and the heterocyclic rings or ring systems in which the heteroatom is in a neutral oxidation state are the reduced forms of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

18. The novel chemiluminescent compound of claim 17 wherein $R^3$ includes at least one substituted six-member ring of the formula

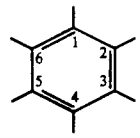

in which the substituents comprise at least one $R^1$ at ring carbons 3, 4 and 5, and $R^2$ and $R^{2'}$ at ring carbons 2 and 6; $R^4$ is directly attached through a covalent bond to the six-member ring at ring carbon 1; $R^3$ is one of phenyl, naphthyl and anthracyl and in those cases where napthyl or anthracyl rings are employed, one of the rings constitutes $R^3$ and the other ring or rings in combination with it are formed via ring carbons thereof other than carbon 1.

* * * * *

UNITED STATES PATENT AND TRADEMARK OFFICE
CERTIFICATE OF CORRECTION

PATENT NO. : 5,284,951

DATED : Feb.08/1994

INVENTOR(S) : Frank Mc Capra

It is certified that error appears in the above-identified patent and that said Letters Patent is hereby corrected as shown below:

On the the title page, add-- Harlen Koelling, Waverly, Iowa--.

Signed and Sealed this

Twentieth Day of September, 1994

Attest:

BRUCE LEHMAN

Attesting Officer

Commissioner of Patents and Trademarks